United States Patent
Fitzgerald et al.

(10) Patent No.: US 12,092,596 B2
(45) Date of Patent: Sep. 17, 2024

(54) METHODS, DEVICES AND SYSTEMS FOR QUANTIFYING BIOMARKERS

(71) Applicants: Colgate-Palmolive Company, New York, NY (US); Rutgers, the State University of New Jersey, New Brunswick, NJ (US)

(72) Inventors: Michael Fitzgerald, Oakhurst, NJ (US); Shamim Ansari, Princeton, NJ (US); Zhongtian Lin, New Brunswick, NJ (US); Jianye Sui, New Brunswick, NJ (US); Mehdi Javanmard, New Brunswick, NJ (US); Donghui Wu, Bridgewater, NJ (US)

(73) Assignee: Colgate-Palmolive Company, Piscataway, NJ (US)

( * ) Notice: Subject to any disclaimer, the term of this patent is extended or adjusted under 35 U.S.C. 154(b) by 813 days.

(21) Appl. No.: 17/250,026

(22) PCT Filed: May 31, 2019

(86) PCT No.: PCT/US2019/035032
§ 371 (c)(1),
(2) Date: Nov. 6, 2020

(87) PCT Pub. No.: WO2019/232461
PCT Pub. Date: Dec. 5, 2019

(65) Prior Publication Data
US 2021/0223234 A1 Jul. 22, 2021

Related U.S. Application Data

(60) Provisional application No. 62/679,149, filed on Jun. 1, 2018.

(51) Int. Cl.
  *G01N 27/02* (2006.01)
  *G01N 33/543* (2006.01)
  *G01N 33/68* (2006.01)

(52) U.S. Cl.
  CPC ......... *G01N 27/02* (2013.01); *G01N 33/5438* (2013.01); *G01N 33/6803* (2013.01); *G01N 27/028* (2013.01)

(58) Field of Classification Search
  None
  See application file for complete search history.

(56) References Cited

U.S. PATENT DOCUMENTS

| | | |
|---|---|---|
| 6,437,551 B1 | 8/2002 | Krulevitch et al. |
| 2009/0051372 A1 | 2/2009 | Sethu et al. |
| 2010/0075340 A1 | 3/2010 | Javanmard et al. |

(Continued)

FOREIGN PATENT DOCUMENTS

| | | |
|---|---|---|
| CN | 102175873 | 9/2011 |
| WO | 2011/029794 | 3/2011 |

OTHER PUBLICATIONS

International Search Report and the Written Opinion of the International Searching Authority issued in International Application PCT/US2019/035032 mailed Oct. 7, 2019.

(Continued)

*Primary Examiner* — J. Christopher Ball

(57) ABSTRACT

Described herein are methods, systems and devices for rapidly detecting biomarkers in a biological sample.

17 Claims, 14 Drawing Sheets

(56) References Cited

U.S. PATENT DOCUMENTS

| | | |
|---|---|---|
| 2011/0160070 A1 | 6/2011 | Gervais et al. |
| 2012/0142032 A1* | 6/2012 | Morgan ............... G01N 33/585 |
| | | 435/287.2 |
| 2012/0244630 A1 | 9/2012 | Svendsen et al. |
| 2013/0183243 A1* | 7/2013 | LaBelle ............. G01N 33/6869 |
| | | 424/9.1 |
| 2016/0299052 A1* | 10/2016 | Koser .................. G01N 27/128 |
| 2018/0059103 A1 | 3/2018 | Saxena et al. |

OTHER PUBLICATIONS

Lin et al., 2015, "PicoMolar level detection of protein biomarkers based on electronic sizing of bead aggregates: theoretical and experimental considerations", Biomedical Microdevices 17(6):1-7.

* cited by examiner

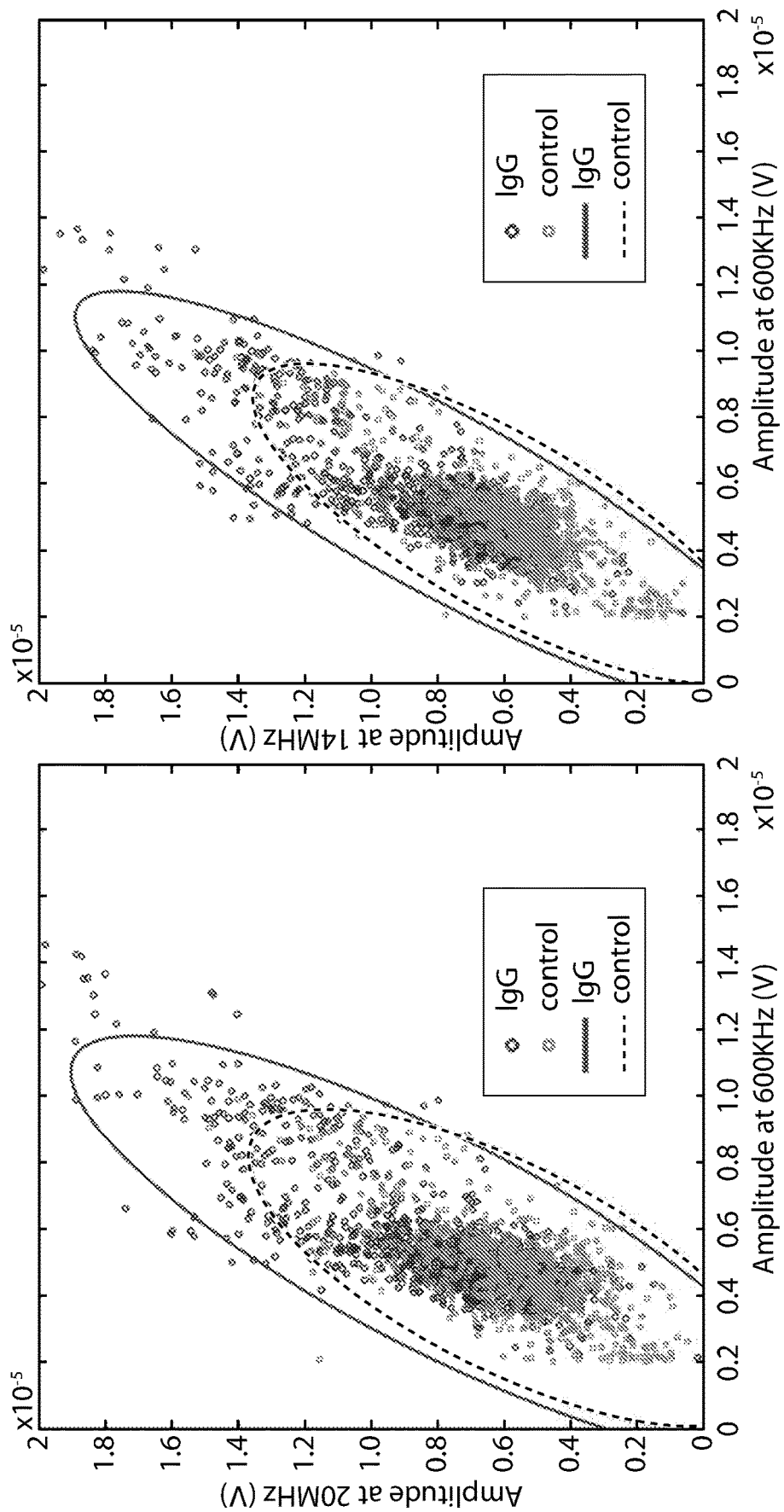

METHODS, DEVICES AND SYSTEMS FOR QUANTIFYING BIOMARKERS

CROSS REFERENCE TO RELATED APPLICATIONS

The present application claims the benefit of and priority to International Application No. PCT/US2019/035032 filed May 31, 2019, which claims the benefit of and priority to U.S. Provisional Patent Application No. 62/679,149 filed Jun. 1, 2018, the contents of which are hereby incorporated herein by reference, in their entirety.

BACKGROUND

Biosamples (such as bodily fluids and tissue) may be used as a diagnostic tool. For example, biofluids may be used to monitor a health status, an onset and progression of a disease, and a treatment progress. The state of various disease can be diagnosed by monitoring the level of certain protein biomarkers in a biofluid. For example, in the case of some chronic diseases related to hepatitis B virus (HBV) and hepatitis C virus (HCV), antibodies may exist in a biofluid sample. In addition, auto-immune disease like sepsis may have biomarkers in a biofluid. Current technologies for performing biomarker assays typically involve bulky instrumentation using optical technologies like sandwich ELISA or protein microarrays. It is therefore desired to have a lightweight, sensitive, inexpensive, and/or compact platform for biofluid diagnosis for the detection and/or determination of diseases, disorders, and other conditions.

BRIEF SUMMARY

The present disclosure may be directed, in one aspect, to a method for identifying a presence of a biological sample. A solid support may be adapted to increase the solid support's affinity for a biomarker associated with a disease, disorder, and/or condition. The solid support and the biological sample may be mixed to form a test sample. The test sample may be inserted into a channel of a platform. The platform may include a first electrode and a second electrode. An impedance of the test sample may be based, for example, based on the signal being sent by the first electrode and being received by the second electrode when the test sample is located adjacent to the first and second electrodes. An amount of a biomarker associated with a disease, disorder, and/or condition may be determined based on the determined impedance of the test sample.

In an aspect, a biochip may be provided. The biochip may include a channel comprising an inlet for receiving a test sample. The test sample may include a biological sample. The biochip may include a first and second electrode positioned adjacent to the channel. The first electrode may be configured to send a signal and the second electrode may be configured to receive the signal. The biochip may include a processor. The processor may be configured to determine an impedance value based on the signal being sent by the first electrode and/or being received by the second electrode when the test sample is located adjacent to the first and second electrodes.

In an aspect, a system may be provided. The system may include a mixing device. The mixing device may be configured to mix a solid support and a biological sample to form a test sample. The system may include a biochip. The biochip may include a channel including an inlet for receiving the test sample. The biochip may include a first and second electrode positioned adjacent to the channel. The first electrode may be configured to send a signal and/or the second electrode may be configured to receive the signal. The system may include a processor. The processor may be configured to determine an impedance value based on the signal being sent by the first electrode and being received by the second electrode when the test sample is located adjacent to the first and second electrodes. The processor may further be configured to determine an amount of a biomarker associated with at least one of a disease, disorder, or condition based on the determined impedance of the test sample.

BRIEF DESCRIPTION OF THE DRAWINGS

The present disclosure will become more fully understood from the detailed description and the accompanying drawings, wherein:

FIGS. 7A, 7B show example scatter plots for voltage peak intensities at 600 kHz, 20 MHz, and 14 MHz.

DETAILED DESCRIPTION

Figure 1A:
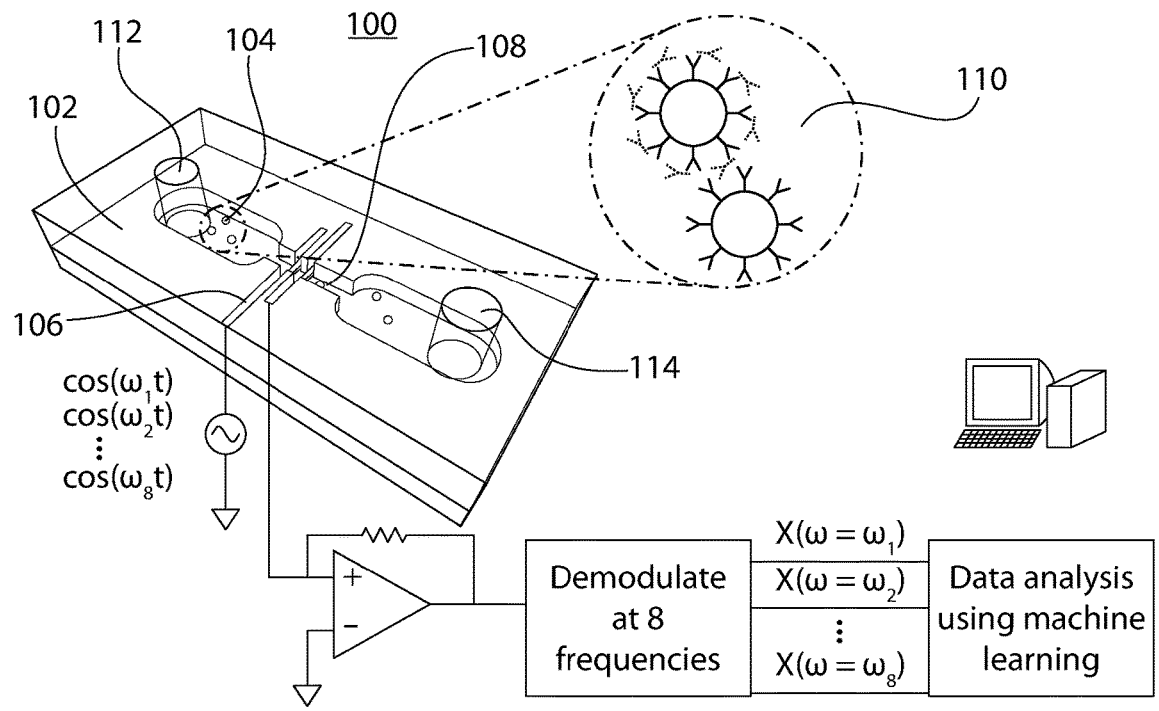
FIG. 1A shows an example system for quantifying one or more biomarkers, as described herein.

The following description of the preferred embodiment(s) is merely exemplary in nature and is in no way intended to limit the invention or inventions. The description of illustrative embodiments is intended to be read in connection with the accompanying drawings, which are to be considered part of the entire written description. In the description of the exemplary embodiments disclosed herein, any reference to direction or orientation is merely intended for convenience of description and is not intended in any way to limit the scope of the present inventions. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require a particular orientation unless explicitly indicated as such. Terms such as "attached," "affixed," "connected," "coupled," "interconnected." "secured" and other similar terms refer to a relationship wherein structures are secured or attached to one another either directly or indirectly through intervening structures, as well as both movable or rigid attachments or relationships, unless expressly described otherwise. The discussion herein describes and illustrates some possible non-limiting combinations of features that may exist alone or in other combinations of features. Furthermore, as used herein, the term "or" is to be interpreted as a logical operator that results in true whenever one or more of its operands are true. Furthermore, as used herein, the phrase "based on" is to be interpreted as meaning "based at least in part on," and therefore is not limited to an interpretation of "based entirely on."

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Features of the present inventions may be implemented in software, hardware, firmware, or combinations thereof. The computer programs described herein are not limited to any particular embodiment, and may be implemented in an operating system, application program, foreground or background processes, driver, or any combination thereof. The computer programs may be executed on a single computer or server processor or multiple computer or server processors.

Processors described herein may be any central processing unit (CPU), microprocessor, micro-controller, computational, or programmable device or circuit configured for executing computer program instructions (e.g., code). Various processors may be embodied in computer and/or server hardware of any suitable type (e.g., desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc.

Computer-executable instructions or programs (e.g., software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to as a "programmable device", or "device", and multiple programmable devices in mutual communication may be referred to as a "programmable system." It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g., internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present inventions may be embodied in the form of computer-implemented processes and apparatuses such as processor-based data processing and communication systems or computer systems for practicing those processes. The present inventions may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

A biosample (e.g., blood, saliva, urine, exhaled breath condensate, tissue, etc.) may be used as a diagnostic tool. For example, a biosample (such as a biofluid) may be used as a diagnostic tool due to its ability to correlate to a health status and/or condition of an animal (such as a person). The health condition may relate to a disease, disorder, or other condition. For example, a biofluid may be used to diagnose and/or determine an onset of a disease, progression of the disease, and/or treatment progress of the disease. A biofluid may be used as a diagnostic fluid in a noninvasive and/or invasive manner. For example, in some examples a biofluid may be provided in such noninvasive ways as via a swabbing of a mouth, a spitting of saliva from the mouth, or a urination. In other examples a biofluid may be provided in such invasive ways as via a taking of blood via a needle, a removal of tissue, etc. Detection (e.g., rapid detection) of antibodies in biofluids (such as saliva) may be performed rapidly and via compact tools (such as via a toothbrush, mouthguard, patch, etc.). The detection of a disease, disorder, or other condition via a biofluid may enable point-of-care diagnosis for diseases, disorders, or other conditions. Although the disclosure may provide many examples relating to biofluids, it should be understood that such examples are for illustration purposes only. The examples may extend to any biosample, including a biofluid as well as a biological tissue, for example.

As described herein, an electronic assay may be used to quantify a biomarker in a biofluid (e.g., blood, saliva, urine, etc.). The biomarker may be associated with a disease, disorder, and/or condition. For example, a biomarker may indicate a presence of a disease, disorder, and/or condition. A biomarker may indicate a risk of (e.g., risk of developing) a disease, disorder, and/or condition. The electronic assay may use an impedance, such as impedance cytometry, to quantify the biomarker in a biofluid. A biomarker may include a protein. A biomarker may include an immunoglobulin G (IgG) and/or immunoglobulin A (IgA). Quantification of a biomarker within a biofluid may be performed within a short period of time (e.g., within 5 minutes, within two minutes, etc.) and via compact, lightweight, and/or inexpensive equipment. In embodiments, machine learning techniques (such as supervised machine learning techniques) may be used to determine (e.g., assist in determining) the quantification of biomarkers (such as immunoglobulins) within a biofluid.

Referring to the figures, FIG. 1A shows an example system 100 for quantifying one or more biomarkers within a biofluid. As described herein, a biomarker may be a protein, such as an immunoglobulin (e.g., IgG and IgG). System 100 may include a biochip 102 that may receive and/or house one or more support structures. Support structures may be a structure in which a biomarker may bind to. For example, support structures may be one or more beads 104. Beads 104 may be formed in one or more configurations (e.g., shapes), such as a circle, square, triangle, etc. Biochip 102 may include one or more channels 108. The support structures (e.g., beads 104) may flow through a channel 108, for example, from one direction to another direction. The beads 104 may flow through the channel via a fluid, such as a micro-fluid.

When flowing through the channel 108, the beads may flow adjacent to (e.g., through, near, between) two or more electrodes, such as electrodes 106. The electrodes 106 may present (e.g., send) an electrical signal to (e.g., near, at) the beads, as described herein. One or more electrodes may receive the signal. The electrode(s) that receive the signal may be the same as the electrode(s) that send the signal, or the electrode(s) that receive the signal may be different than the electrode(s) that send the signal. The signal received by the one or more other electrodes may be affected by the beads and/or the biomarker coupled (e.g., attached) to the beads. For example, a bead without any biomarker (e.g., biomarker coupled to the bead) may have an impedance (e.g., an impedance signature). A bead with one or more biomarkers (e.g., biomarkers coupled to the bead) may have an impedance (e.g., an impedance signature). The impedance (e.g., impedance signature) of the bead without any biomarker coupled may be different than the impedance (e.g., impedance signature) of the bead with a biomarker coupled. The difference(s) of one or more of the impedances may be determined. For example, a difference of the impedances (e.g., impedance signatures) of the bead with a biomarker coupled and the bead without a biomarker coupled may be determined. The difference(s) of the impedances may be used to determine and/or identify a bead with a biomarker coupled and the bead without a biomarker coupled. The difference(s) of the impedances may be used to determine the amount, type, weight, etc. of the biomarker coupled to a bead.

As described herein, the signal received by the electrode(s) may be affected by the amount, type, weight, etc., of the biomarker coupled to the beads. The signal received may be used to determine the impedance value. For example, the signal received may be a representation of the impedance value. As described herein, the impedance value may be used to determine the amount of biomarker coupled to one or more beads. The amount of biomarker coupled to one or more beads may be used to determine the amount of biomarker associated with (e.g., located within) a biofluid, such as saliva, sweat, exhaled breath condensate, tissue, urine, and/or blood. As a result, in examples the impedance value may be used to quantify the amount of biomarker within a biofluid.

Beads 104 may enter the channel 108 of biochip 102 via one or more inlets and exit biochip via one or more outlets, such as inlets 112 and/or outlets 114. Although the inlet 112 and outlet 114 are shown on respective left and right sides of the biochip 102, it should be understood that such a configuration is for illustration purposes only and one or more inlets and outlets may be formed on any portion of the biochip that allows the beads 104 to enter and/or exit the channel 108.

A biomarker may be added to (e.g., mixed with, coupled to, etc.) beads 104. For example, a biomarker associated with (e.g., located within) a biofluid may be mixed with beads 104. Beads 104 may be adapted (e.g., configured) to capture a biomarker (such as soluble IgG/IgA (target antigen) molecules) found in a biofluid. Such biofluids may be blood, saliva, urine, etc., as described herein. Beads 104 may be adapted to capture a biomarker by providing a coating to the beads. For example, the beads may be coated with a biomarker, such as a protein. The beads 104 may be magnetic anti-IgG/anti-IgA (primary antibody) coated beads. Anti-IgG/anti-IgA (detector antibody) may be added to (e.g., coated upon) the beads 104. Anti-IgG/anti-IgA (detector antibody) may be added to the beads 104 to increase the effective radius of the bead-protein complex, as shown in blown-up image 110.

Figure 1B:
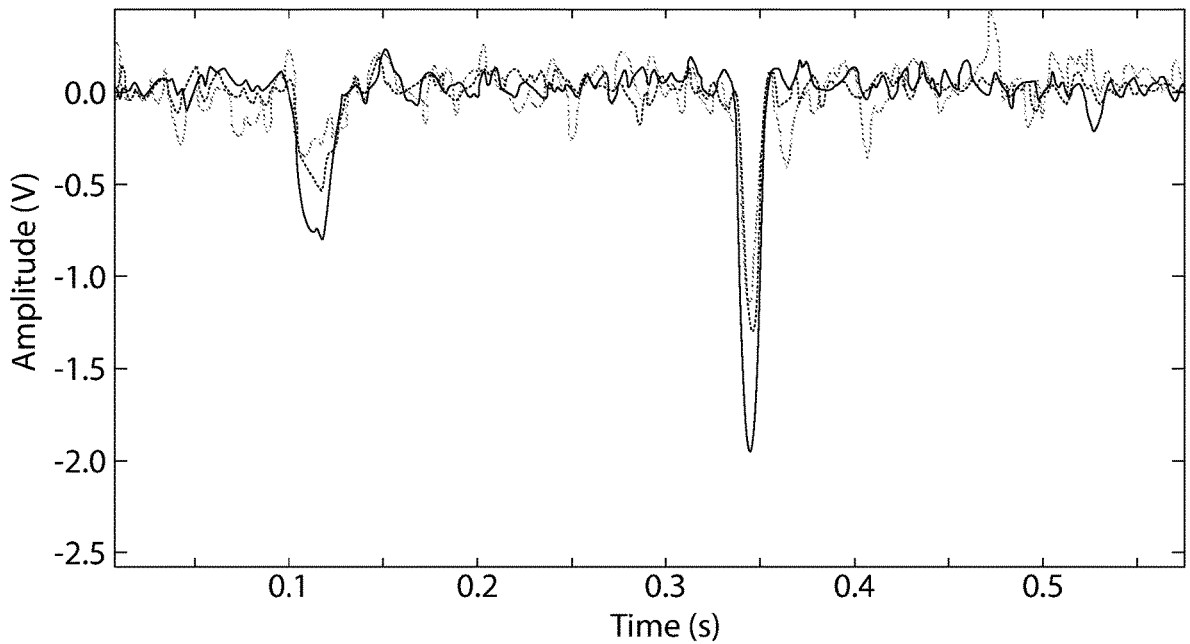
FIG. 1B shows example wavelengths related to eight frequencies, as described herein.
Figure 5:
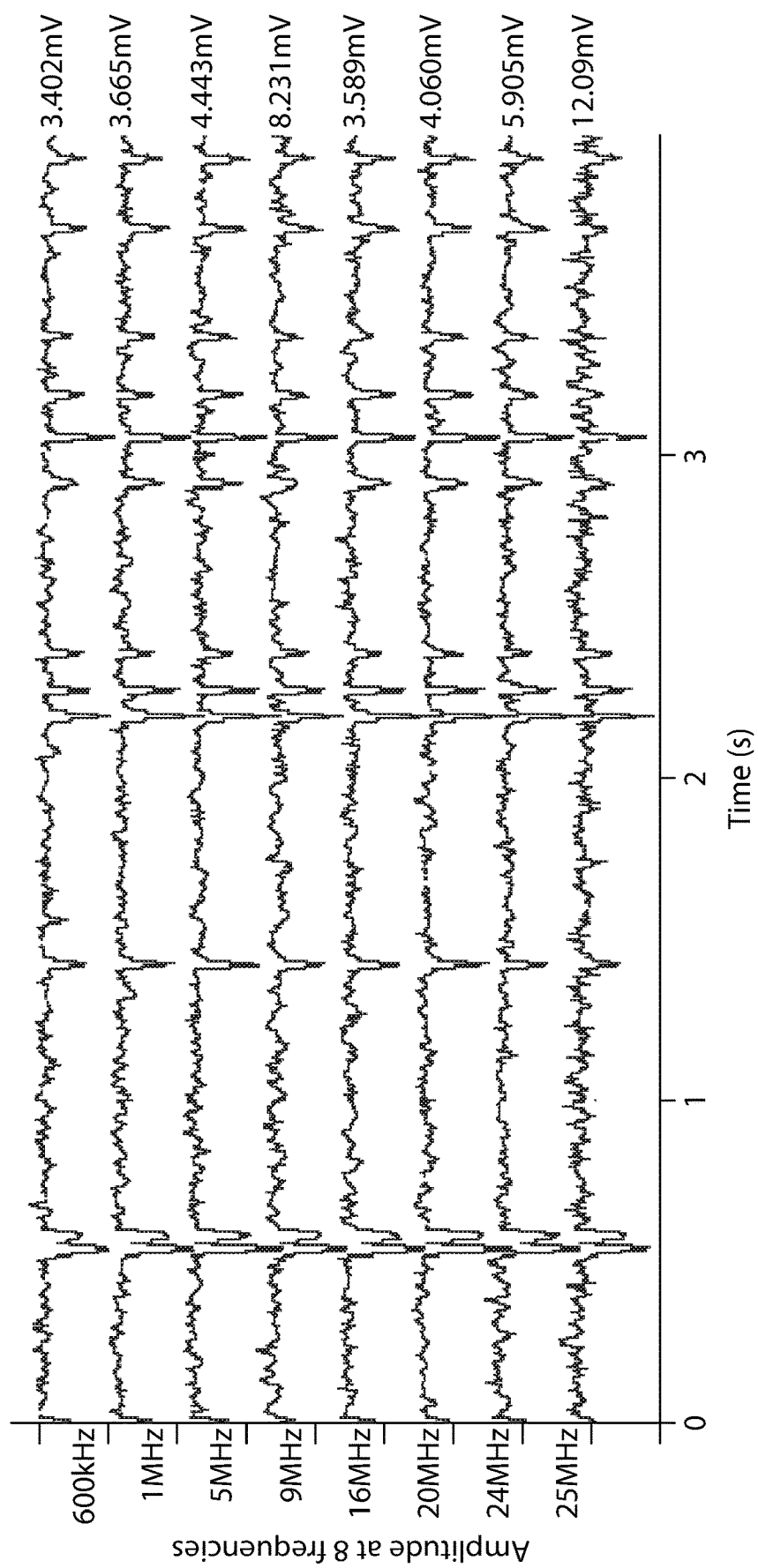
FIG. 5 shows example wavelengths representing beads passing through an impedance device.

The beads 104 may flow through a device (e.g., an impedance cytometer) that may probe the impedance of the beads. For example, the impedance cytometer may probe the impedance of the beads at one or more (e.g., eight) frequencies. Eight example frequencies are shown on FIG. 1B. As shown on FIG. 1B, the frequencies may have one or more peaks. The peaks shown on FIG. 1B include data (e.g., raw data) representing beads 104 that have passed over the electrodes. Example frequencies may be 600K, 5M, 21M. Example amplitudes (e.g., of the input AC voltage) may be 400 mV. FIG. 5 shows other example wavelengths. For example, FIG. 5 shows other data (e.g., raw data) representing beads being adjacent to (e.g., passing through) an impedance cytometer at eight frequencies. The frequencies shown on FIG. 5 include 600 kHz, 1 MHz, 5 MHZ, 9 MHz, 16 MHz, 20 MHz, 24 MHz, and 25 MHz, although other frequencies may be used. The amplitudes of the Input AC Voltage may be 400 mV, although other amplitudes may be used.

The use of impedance cytometry (e.g., multi-frequency electrical impedance cytometry) may allow for electronically determining the level to which beads have captured biomarkers in a biofluid, such as target IgG/IgA molecules in saliva. In examples, machine learning techniques may also, or alternatively, be used to determine the level to which beads have captured a biomarker (such as target IgG/IgA molecules) in a biofluid. Example machine learning techniques may include one or more of a linear-output regression model, a support vector regression model, decision trees, supervised nonlinear regression, nearest neighbor algorithm, association rule learning, inductive logic programming, reinforcement learning, representation learning, similarity learning, sparse dictionary learning, manifold learning, dictionary learning, boosting, Bayesian networks, case-based reasoning, Kernel machines, subspace learning, Naive Bayes classifiers, ensemble learning, statistical relational learning, a nonlinear Gaussian process regression model (which is capable of operating on pixel/voxel data directly), and the like.

It may be determined (e.g., confirmed) whether binding occurred (e.g., properly occurred) in one or more ways. For example, it may be determined (e.g., confirmed) whether binding occurred by machine learning, as described herein. It may be determined whether binding occurred via a visual inspection, an electronic inspection, etc. For example, it may be determined whether binding occurred via fluorescently tagging (FITC) the beads, such as the IgG/IgA bound beads. The fluorescently tagged beads may be observed (e.g., observed optically) to determine whether a binding (e.g., a proper binding) occurred.

Figure 2A:
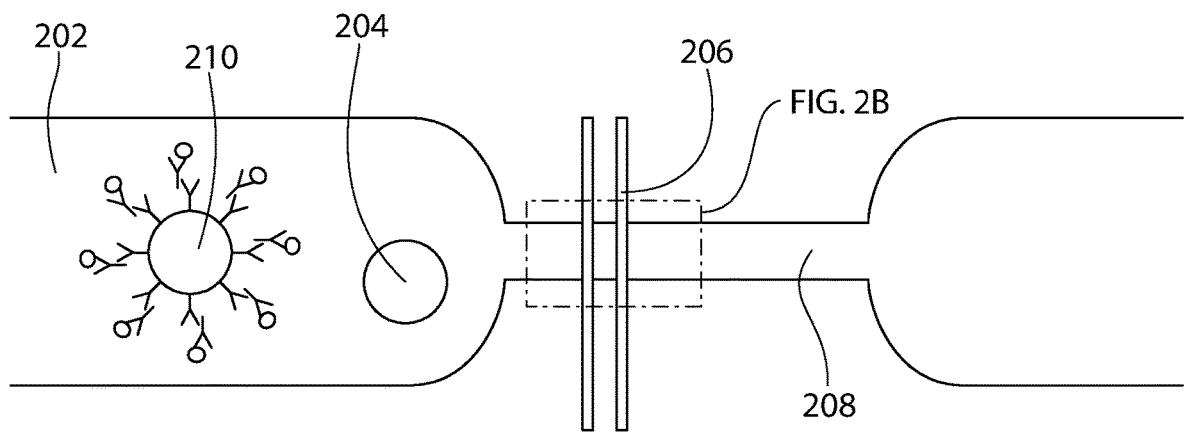
FIG. 2A shows a blown-up depiction of an example biochip.

FIG. 2A shows a schematic of an example biochip, such as biochip 202. Biochip 202 may be similar to biochip 102, shown on FIG. 1A. Biochip 202 may be a microfabricated biochip that may consist of one or more (e.g., two) electrodes, such as electrodes 206. Electrodes 206 may be formed of one or more metals, such as gold. Electrodes 206 may be coupled to and/or formed on a glass substrate. Electrodes 206 may be coupled to and/or formed on a glass substrate with a channel, such as channel 208. The channel 208 may be formed above the substrate. The channel 208 may be a PDMS (Polydimethyl Siloxane) channel.

To fabricate electrodes 206, a photolithography may be applied on a 3-inch fused silica wafer. The photolithography may be an optical lithography or ultraviolet (UV) lithography, in examples. For example, the photolithography may be used in the microfabrication to pattern parts of the thin film and/or the bulk of the substrate (e.g., substrate, or wafer, of biochip 202). A photo-patterning on a fused silica wafer may be performed. Evaporation may be performed, such as electron beam metal evaporation. A lift off may be performed. The photo-patterning may include cleaning the substrate/wafer, spin coating photoresist, photoresist soft baking, ultra-violet exposure (e.g., through a 4-inch chromium mask), resist development, and/or hard baking. 5 nm of chromium may be deposited on the substrate/wafer, for example, via evaporation (such as the electron beam evaporation described herein). 5 nm of chromium may be deposited on the substrate/wafer for enhancing the adhesion of the layer (e.g., 100 nm gold layer) to the substrate/wafer which was deposited. Lift off may be performed using a cleaner (e.g., ultrasonic cleaner), for example, in acetone.

Figure 2B:
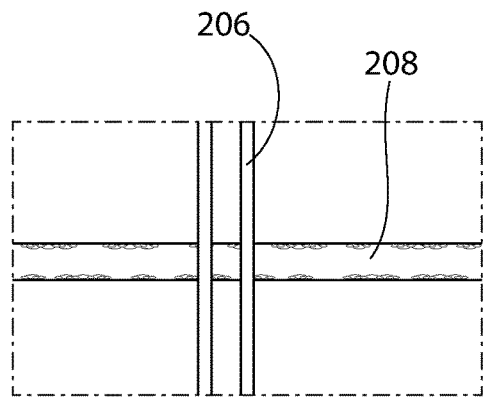
FIGS. 2B, 2C, and 2D show example channels within a biochip, such as the biochip shown in FIG. 2A.

The channel 208 may be a micro-channel. FIG. 2B shows a blown-up version of channel 208, as shown on FIG. 2A. Channel 208 may have varying dimensions, such as varying widths and/or heights. For example, channel 208 may be 300 µm wide and/or 20 µm high. The channel 208 may narrow. For example, channel 208 may narrow to be 30 µm wide and/or a 20 µm high sensing pore. The cross-sectional area of the sensing pore (e.g., smaller cross-sectional area of the sensing pore) may permit focusing of particles and/or a higher electrical sensitivity. Beads (such as 2.8 µm IgG and/or anti-IgG FITC bind beads and/or 2.8 µm beads) may be detected at a bead level (e.g., a single bead level).

The electrodes (such as electrodes 206) may have varying dimensions (such as varying widths and/or lengths) and/or spacings. For example, the spacing between the two electrodes 206 may be 20 µm and/or the width of an (e.g., each) electrode may be 15 µm. A support structure (e.g., a solid support) may be adjacent to the electrodes 206. The support structure may be a bead, such as a bead carrying a biomarker as a result of being mixed with a biofluid. The bead may be placed adjacent to the electrodes via a force, such as a force provided via a pump, gravity, internal/external pressure, or the like. The bead adjacent to the electrodes may be a bead 204, which may be carrying (e.g., housing, coupled to, etc.) a biomarker (bead 210). The biomarker may be a protein, such as IgG and/or IgA. Bead 210 may be adjacent to one or more electrodes 206 and/or bead 210 may pass through (e.g., between) two or more electrodes. The electrode(s) may send a signal and receive a signal. The received signal (e.g., the value of the received signal) may be based on the presence (or absence) of a biomarker associated with (e.g., coupled to) the bead 210, as described herein.

Figure 2C:
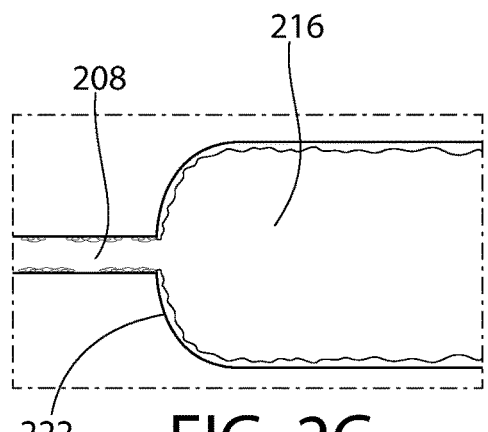
Figure 2D:
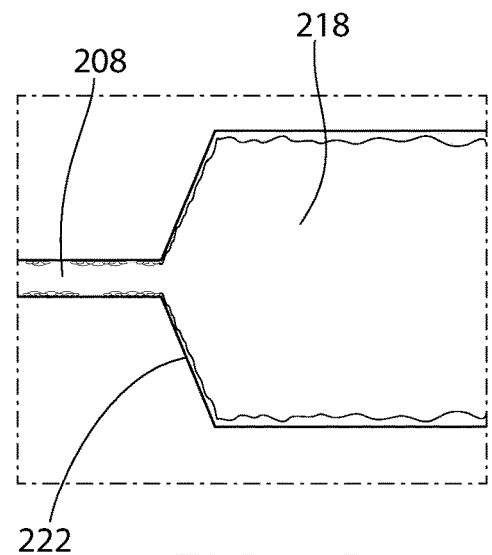

A channel, such as channel 208, may include one or more configurations and/or one or more paths (e.g., channels within the channel). FIGS. 2C and 2D show examples of channels 208 that may be formed within a biochip (such as biochip 202, shown in FIG. 2A), although the examples shown on FIGS. 2C and 2D are for illustration purposes only and other channel configurations may be used. FIG. 2C shows channel 208 forming into well 216. As can be seen on FIG. 2C, a single well 216 may be wider than channel 208, although one or more wells 216 may be in contact with channel 208 in other examples. Further, although well 216 shown on FIG. 2C has curved (e.g., rounded) edges 222, other configurations of well 216 may be used. For example, FIG. 2D shows an example in which channel 208 forms into a well 218 having linear edges 222. As shown on FIGS. 2C and 2D, the well may be wider than channel 208, although in other examples the well may be thinner than the channel, there may be more (or less) wells than there are channels, etc.

Figure 3:
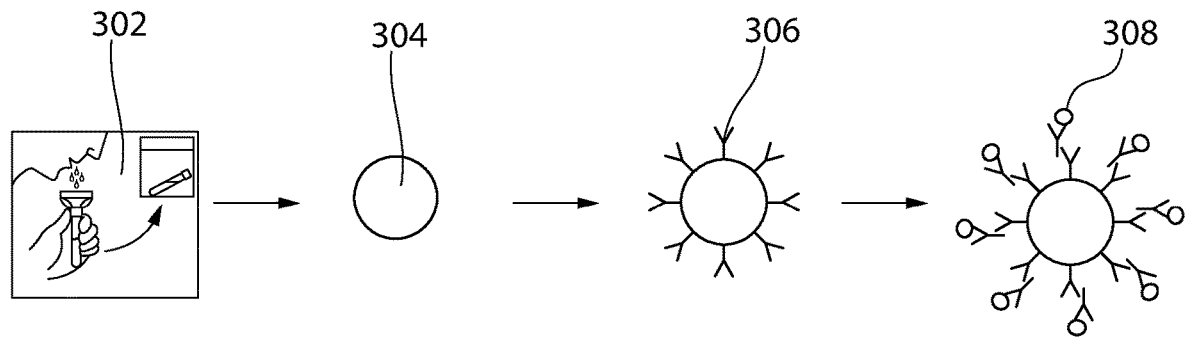
FIG. 3 shows example assay steps, as described herein.

FIG. 3 illustrates a pictorial view of example assay steps. Assay steps may relate the use of a mixing device and/or a biochip, as described herein. Assay steps may relate to a biofluid and/or a biomarker, as described herein. As an example, assay steps may relate to a biofluid (e.g., saliva, blood, urine) and/or a biomarker, such as an IgG, IGA, or one or more other immunoglobulins. At 302, a biofluid (e.g., saliva) may be provided. The biofluid may be provided in a non-invasive way (e.g., via a spitting of saliva, a swab of an orifice, a collection of urine, etc.) and/or in an invasive way (e.g., via a needle).

A support structure (e.g., solid support) may be used to couple to a biomarker of the biofluid. For example, one or more types of beads may be used to couple to a biomarker of the biofluid, at 304. The beads may be adapted to couple to one or more biomarkers. The beads may be adapted to increase the beads' affinity for a biomarker. In examples, the beads may be said to be functionalized to couple to one or more biomarkers. For example, a bead may be coated, at 306. Coating the bead may permit (e.g., assist) the beads to couple to one or more biomarkers. As an example, 2.8 µm beads (e.g., paramagnetic Dynal beads) may be coated with a coating material. The coating material may be anti-mouse IgG antibodies. The beads may be coated with anti-mouse IgG antibodies so that the beads may capture the mouse IgG in the biofluid (e.g., saliva) sample, at 308. For IgG, biofluid (e.g., saliva) samples may be spiked with mouse IgG at one or more concentrations, such as concentrations of 1667 nM, 167 nM, and/or 17 nM.

An assay (e.g., a 2-minute assay) may be performed as described herein. For example, a support structure (e.g., beads, such as sheep anti-mouse IgG beads) may be washed (e.g., washed three times). The beads (e.g., IgG beads) may be washed in PBS 0.1% BSA.

Figure 6A:
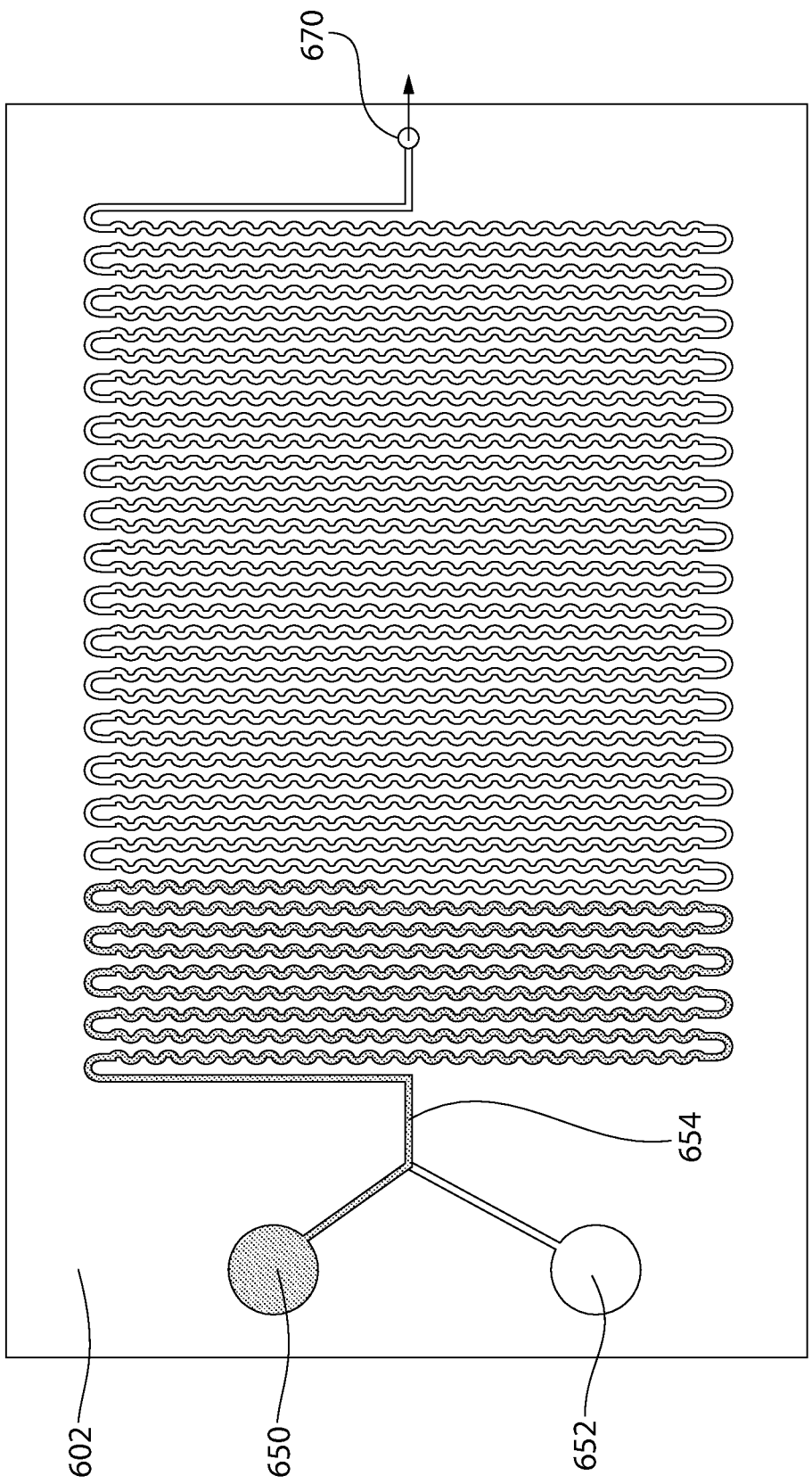
FIG. 6A shows an example device for mixing a bead, biofluid, and/or biomarker, as described herein.

The beads may be mixed with a biofluid (such as a biomarker spiked biofluid) via a mixing device, such as example mixing device 602 shown on FIG. 6A. Mixing may dilute the biofluid (e.g., saliva) and/or mixing may perform a filtering. For example, mixing may filter particles (e.g., large particles) from the biofluid. Mixing may mix the biofluid (e.g., the biomarker in the biofluid) with the beads. For example, the beads may be mixed with mouse IgG spiked saliva via exampling mixing device 602.

Mixing device 602 may comprise one or more inlets for accepting a support structure (e.g., beads), a biomarker, and/or a biofluid. For example, inlet 650 may accept one or more beads. The beads may be adapted (e.g., functionalized) beads, such as beads coated with anti-mouse IgG antibodies. Inlet 652 may accept a biofluid, such as saliva, blood, urine, etc. The biofluid may include a biomarker, as described herein. In an example, the beads may be mixed with a protein (e.g., mouse IgG) off chip, although the beads may also, or alternatively, be mixed on chip. One or more of the inlets may flow into one or more channels. For example, inlet 650 and/or inlet 652 may flow into channel 64.

Beads may be mixed with a biofluid (e.g., saliva) in channel 654, beads may be mixed with a biomarker (e.g., IgG, such as mouse IgG) in channel 654, a fluid (e.g., a biofluid, such as saliva) may be filtered in channel 654, etc. Mixing device 602 may include one or more outlets, such as outlet 670. Outlet 670 may be used to expel (e.g., release) the portions mixed on the mixing device 602. For example, outlet 670 may be used to expel the beads mixed with the biofluid (e.g., the biomarker found in the biofluid). In examples in which filtering is performed, an outlet may be used to expel one portion (e.g., the beads mixed with the biofluid) and one or more outlets may be used to expel the filtered materials.

Figure 6B:
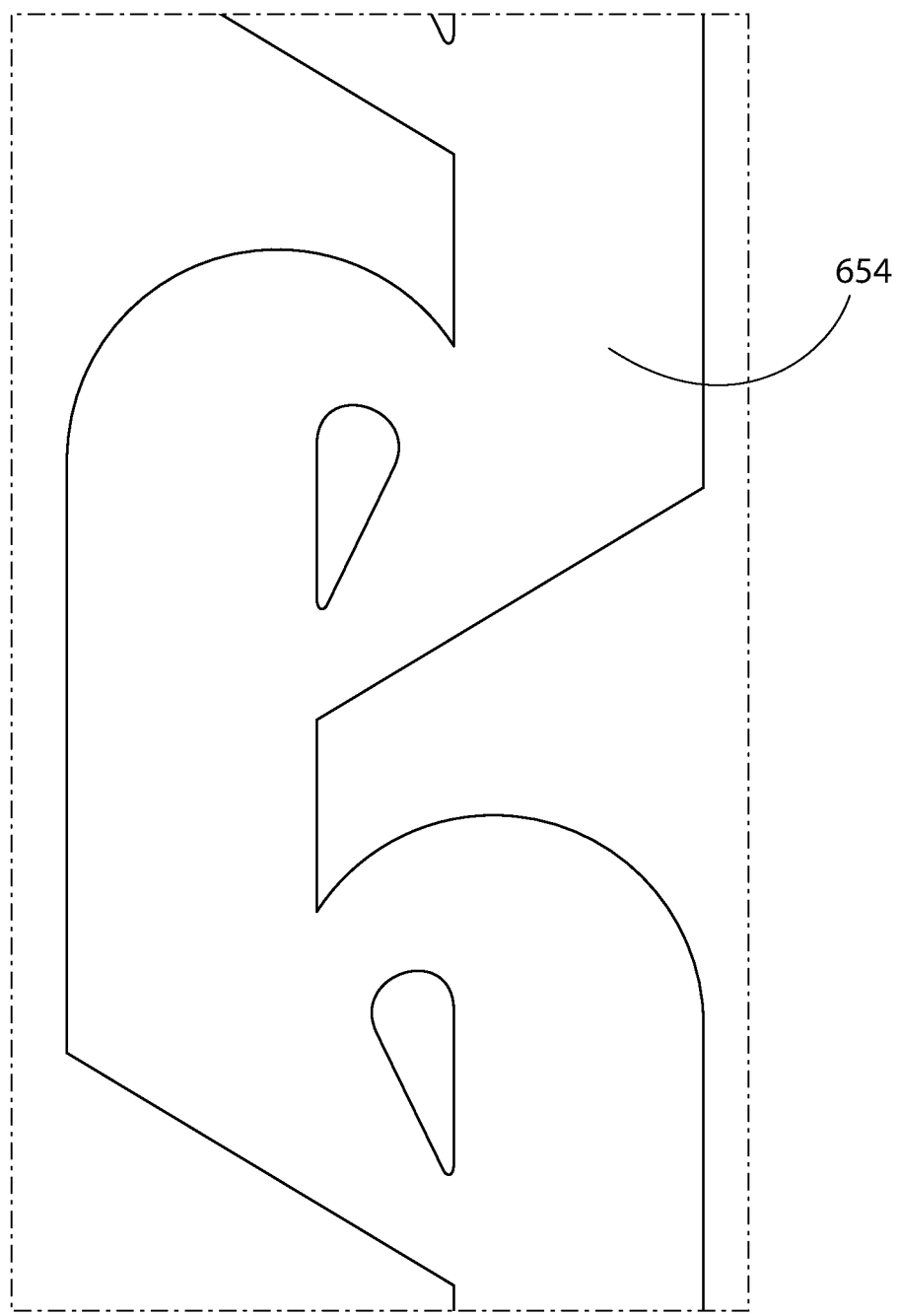
FIGS. 6B, 6C show example blown up versions of the channel of the example device for mixing a biomarker with a biofluid, as described herein.
Figure 6C:
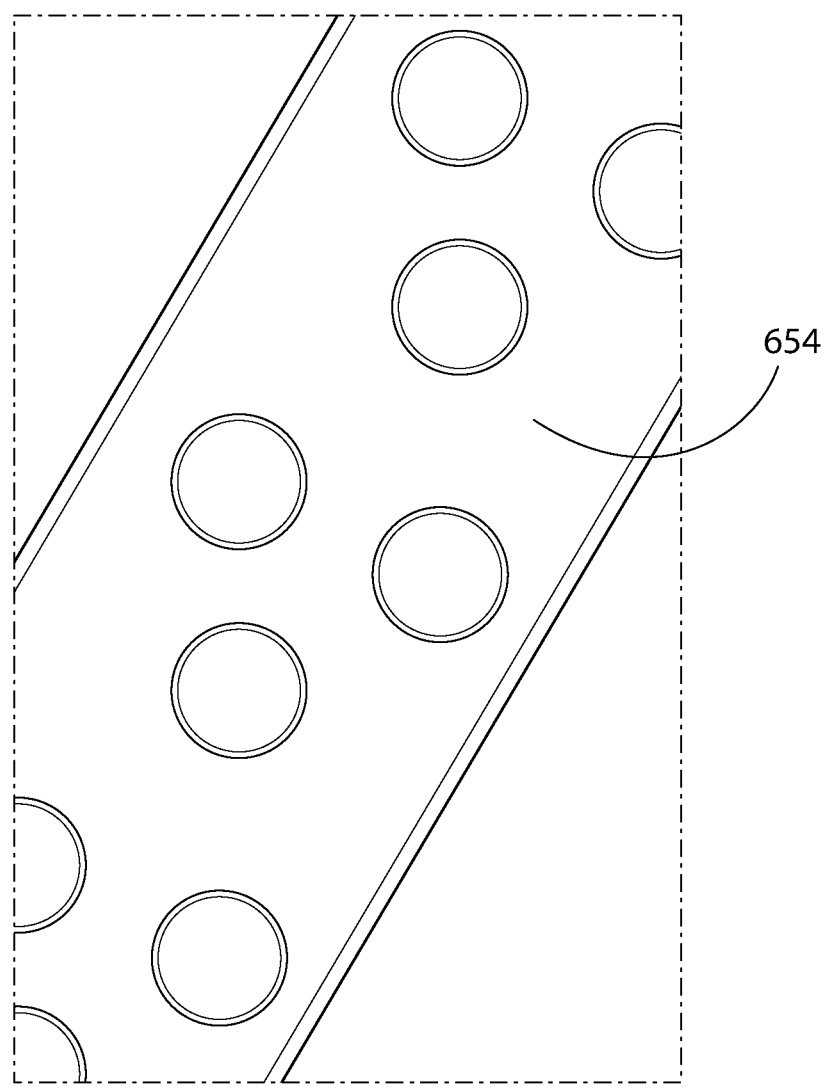
Figure 7C:
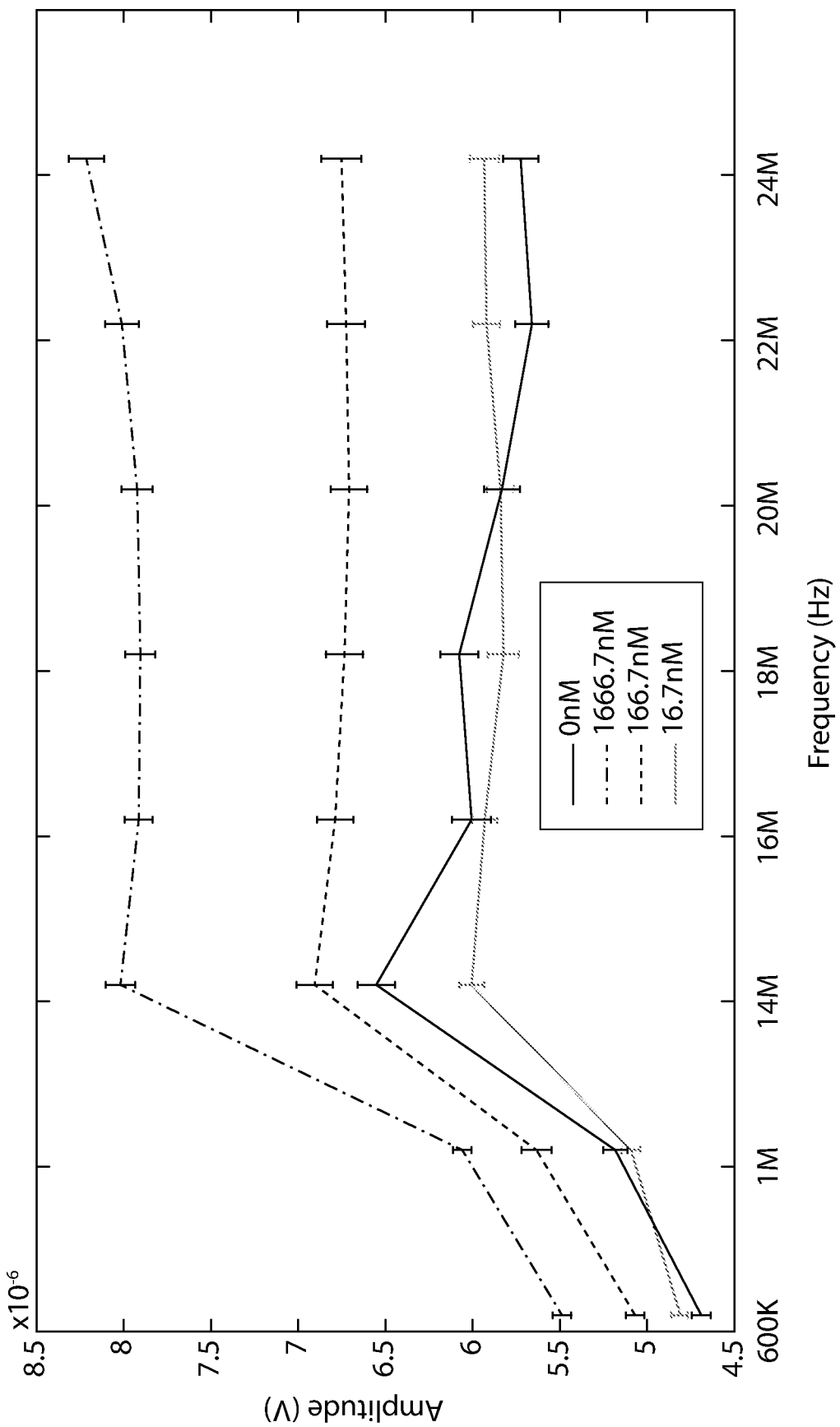
FIG. 7C shows an example plot of amplitudes based on a frequency for a plurality of concentrations.

Channel 654 may be an epindorph tube, in an example. The channel 654 may be formed in one or more of a variety of configurations. For example, channel 654 may form a tesla structure, such as the tesla structure shown on FIG. 6B. In an example, channel 654 may form a pillar structure, such as the pillar structure shown on FIG. 6C. The channel may be used for mixing of the beads with the biofluid (e.g., the biomarker in the biofluid). The channel may be used for filtering, as described herein. For example, pillars of the pillar structure (shown on FIG. 6C) may be used for filtering (e.g., filtering large particles of a fluid, such as a biofluid). A channel may be used for mixing or the channel may be used for filtering. In other examples, a channel (e.g., the same channel) may be used for mixing and filtering.

The beads (e.g., the beads mixed with the spiked mouse IgG) may be rotated. For example, the beads (e.g., the beads mixed with the spiked mouse IgG) may be rotated on mixing device 602 (e.g., for 2 minutes). The beads mixed with the spiked mouse IgG may be rotated at 25 degrees Celsius. It may be determined (e.g., confirmed) whether the beads have bound (e.g., have mixed and/or bound properly) with a biomarker. For example, it may be confirmed whether the binding of the beads with the spiked mouse IgG has occurred (e.g., properly occurred). The beads may be washed (e.g., washed three times with PBS 0.1% BSA). The beads may be mixed with tagged anti-IgG. Beads may be washed with PBS to ensure unbound antibodies (e.g., all unbound antibodies) are washed away, for example, before electrical testing.

One or more biofluids may be spiked with a biomarker. For example, for IgA, biofluid (e.g., saliva) samples may be spiked with human IgA. Biofluid (e.g., saliva) samples may be spiked with human IgA at a concentration of 8.4 μM. Beads (e.g., 2.8 μm tosylactivated beads) may be coated with antibodies (such as anti IgA antibodies), for example, to capture the biomarker (e.g., human IgA) in the biofluid (e.g., saliva) sample.

The assay (e.g., the two-minute IgA assay) may be performed as described herein. Beads (e.g., Tosylactivated beads) may be washed (e.g., washed three times) with 1 ml buffer B (0.1 M Na-phosphate buffer. pH 7.4). The beads (e.g., the Tosylactivated beads) may be washed to couple ligands to the beads. The beads may be mixed with antibodies (such as anti IgA antibodies) in a mixing buffer, as described herein. The mixing buffer may consist of 150 μL buffer B and 100 μL buffer C (3 M ammonium sulphate in Buffer B). The beads may be incubated on a roller, for example, at 37 degrees Celsius and/or for 18 hours. The beads may be incubated in buffer D (PBS pH 7.4 with 0.5% (w/v) BSA) for a time, such as for an (e.g., another) hour. The beads may be washed. For example, the beads may be washed with buffer E (PBS pH 7.4 with 0.1% (w/v) BSA) one or more (e.g., three) times. The beads may be ready for coupling with a biomarker, such as human IgA. To couple with the biomarker (e.g., the IgA), the beads (e.g., the pretreated beads) may be mixed with human IgA spiked biofluid (e.g., saliva) samples in the channel (e.g., the epindorph tube) and/or rotated (e.g., rotated for two minutes, e.g., at 37 degrees Celsius). The beads may be washed (e.g., washed three times) and mixed with FITC tagged with anti-IgA. As described herein, the beads may be washed three times with PBS to ensure unbound antibodies (e.g., all unbound antibodies) are washed away before the electrical testing.

Figure 4:
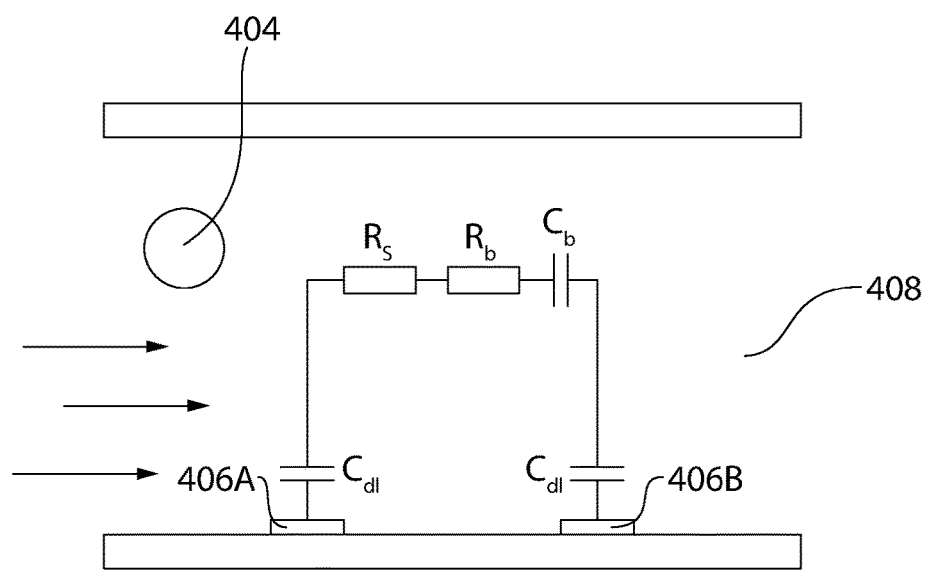
FIG. 4 shows an example circuit including one or more beads and one or more electrodes.

FIG. 4 shows an example circuit 400. Circuit 400 may include a channel, such as channel 408. Channel 408 may be similar to channel 108/208, as shown on FIGS. 1A and 2A. Channel 408 (e.g., micro-channel 408) may begin from a 300 μm wide and 20 μm high channel part. The circuit 400 may include one or more beads 404 and one or more electrodes 406A, 406B. The beads 404 and/or the electrodes 406A, 406B may be located/positioned within channel 408. As described herein, a metal, such as gold, may be used as the material (e.g., the inert material) for one or more of the electrodes 406A, 406B. The circuit 400 may include one or more (e.g., two) Debye layer capacitance ($C_{dl}$) 420 at an (e.g., each) electrode. The Debye layer capacitance ($C_{dl}$) 420 may be located in series with the solution (e.g., micro-fluidic solution) resistance and/or in series with impedance components representing beads, such as beads 404. The beads 404 may comprise a capacitance ($C_b$) at its surface in series with resistance ($R_b$).

$$Z = \frac{2}{j\omega C_{dl}} + R_{solution} + \frac{1}{j\omega C_{bead}} + R_{bead} \qquad \text{(Eq. 1)}$$

An impedance may be determined. For example, an impedance of the bead 404 and/or the biomarker (e.g., the biomarker coupled to the bead) may be determined. The impedance of the bead and/or the biomarker may depend on the size and/or conductivity of the bead 404 and/or the dielectric permittivity at the surface of the bead 404. In examples it may be difficult to detect the binding of the biomarker (such as the IgG and/or IgA) by single or double frequency cytometry changes. For example, it may be difficult to detect the binding of IgG and/or IgA by single or double frequency cytometry changes due to the properties (e.g., small size) of the IgG and/or IgA. Multi-frequency impedance cytometry and/or machine learning techniques may be used to detect the binding of the biomarker (e.g., IgG and/or IgA). In examples, optical inspection may be used to detect the binding of the biomarker, as described herein.

Channel 408 (e.g., micro-channel) may narrow and/or shorten. For example, channel 408 (e.g., micro-channel) may begin as a 300 μm wide and/or 20 μm high channel part and may narrow to 30 μm wide and/or 20 μm high (e.g., may narrow to 30 μm wide and/or 20 μm high sensing pore). A smaller cross-sectional area (e.g., of the sensing pore) may improve the focusing of particles (e.g., above the sensor) and/or may increase electrical sensitivity. The improved focusing of particles (e.g., above the sensor) and/or increased electrical sensitivity may allow the beads (e.g., the 2.8 μm IgG beads and the anti-IgG FITC bind 2.8 μm beads) to be differentiated.

The spacing between the electrodes 406A, 406B may be 30 μm and/or the width of one or more (e.g., each) electrode may be 20 μm. Channel 408 may be formed in silicone, such as Polydimethylsiloxane (PDMS), for example. Channel 408 may be formed from a master mold fabricated using soft lithography. The fabrication may consist of a cleaning of a wafer, spin coating, soft baking, photo-patterning an inverse feature onto a wafer (e.g., a three-inch silica wafer), UV light exposure, development, and/or hard baking. To make the PDMS channels, a pre-polymer and a curing agent may be mixed. The pre-polymer and a curing agent may be mixed at a ratio of 10 to 1. The pre-polymer and curing agent may be poured onto the master mold. After the PDMS is cured (e.g., cured for approximately an hour), the PDMS may be peeled off. The channels may be cut out and/or holes may be punched, for example, to create inlets and outlets. The channel 408 may be aligned to the substrate of the electrodes and/or bonded onto the electrode wafer, for example, by implementing oxygen plasma treatment to one or more (e.g., both) substrates 420A, 420B.

An impedance measurement of one or more support structures (e.g., beads) may be performed, as described herein. For example, an impedance measurement of beads coupled with a biomarker (e.g., a protein, such as an immunoglobulin) may be performed. An impedance measurement of beads with one or more concentrations of IgG/IgA may performed one or more (e.g., three) times. The beads may be caused to flow via a pump, a pressure, etc. For example, the beads may flow without a pump to minimize noise and/or to minimize influences from noises. The channel (such as channel 408) may be treated with a material. For example, the channel may be treated with plasma. The material (e.g., plasma) may cause the channel to be hydrophilic. The channel may be filled with phosphate buffer saline (PBS)<Inventors: please confirm this acronym> to retain the channel's hydrophilicity.

Pressure differences may exist between the inlet and outlet of the biochip. The pressure differences may be caused by the volumes (e.g., different volumes) of buffer at the inlet and outlet. The beads may be injected into the inlet of the biochip. For example, the beads may be injected into the inlet of the biochip because of the pressure differences from the inlet and outlet. The beads may flow adjacent to (e.g., through, between, near, etc.) the multi-frequency impedance sensor which may be connected to a lock-in amplifier (Zurich Instrument HF2 series). The input AC voltage may be 400 mV peak-to-peak and/or the gain may be 1 kV/amp.

As particles (e.g., beads coupled to the biomarkers) pass adjacent to (e.g., near, between, over, etc.) the electrodes, impedance responses at frequencies (e.g., eight discrete frequencies) may be captured. The frequencies may include frequencies from 600 kHz to 25 MHz. A material (e.g., a cover, such as a metal box) may be used to cover the sensor. The cover may be used to decrease the noise(s) during the testing. The recorded data may be processed. For example, the data may be processed using software, such as custom-written MATLAB code. The software may perform detrending, denoising, peak finding, and/or differentiating of the beads that have bound with a biomarker (such as IgG/IgA) from the beads that have not bound with a biomarker. As an example, the software may use machine learning techniques to perform detrending, denoising, peak finding, and/or differentiating of the beads having bound with a biomarker (such as IgG/IgA) from the beads that have not bound with a biomarker. Also, or alternatively, the binding may be electrically and/or optically confirmed. For example, the beads may be observed under a fluorescent microscope after the electronic assay.

A machine learning technique may be performed, as described herein. For example, a machine learning technique may be performed to distinguish the beads that have coupled with a biomarker and beads that have not coupled with a biomarker. Machine learning techniques performed may include supervised machine learning techniques and/or unsupervised machine learning techniques. For example, the machine learning techniques may include a support vector machine (SVM) machine learning rule/algorithm. The machine learning techniques (e.g., the SVM machine learning rules/algorithms) may be performed to improve classification accuracy and/or to detect the differences between anti-IgG beads and beads that have coupled to (e.g., captured) a biomarker, such as IgG.

One or more features may be used for the machine learning techniques. For example, peak amplitude(s) of one or more (e.g., eight) frequencies may be used as features for the machine learning techniques. Classification of a particle type (e.g., biomarker positive or biomarker negative) may improve. For example, classification of a particle type may improve in high-dimensional space(s). The machine learning model (e.g., the SVM model) may be trained using data, such as the frequency data, amplitude data, classification data, impedance data, etc. An entirety of the data (e.g., an entirety of the frequency data, amplitude data, classification data, impedance data, etc.) may be used to train the machine learning model, or a portion of the data may be used. An entirety of the data may be used to test the machine model (e.g., the SVM model) or a portion of the data (e.g., the remaining data after training) may be used for testing the SVM model. The accuracy may be calculated, for example, by comparing the prediction with the true category.

A score, such as a biomarker quantification score, may be generated (e.g., formulated). The biomarker score may be defined as (SVM Accuracy-50)/50, for example. The biomarker score may provide a method (e.g., a self-calibrated method) for quantifying biomarker levels. An example equation for determining a biomarker score may include the following.

$$\text{Biomarker Quantification Score} = \frac{SVM \text{ Accuracy} - 50}{50}$$

The viability and/or repeatability of the assay (e.g., the two-minute assay) may be determined, as described herein. Experiments may be performed to verify the viability and/or repeatability of an assay. The experiments may be performed optically and/or electrically. Experiments may be performed at one or more concentrations of the biomarker (e.g., the protein, such as the IgG/IgA. As an example, for IgG and/or IgA a positive assay may show (e.g., optically show) a stronger florescent signal at a higher concentration. A negative assay may show (e.g., optically show) a black background, for example, as a result of a protein (e.g., a specific) protein fluorescently tagging. Such differences (e.g., differences in images) may be used to confirm whether the IgG/IgA binds to the beads.

A device, such as the biochip, may receive a sample. The sample may be the biomarker (e.g., the IgG/IgA) bound to the support structure (e.g., the beads). The sample may be provided to the biochip in one or more ways, including injecting the sample into the biochip. After the sample is provided to (e.g., injected into) the biochip (e.g., microfluidic biochip), particles (e.g., particles moving via pressure-driven flow) may be caused to be adjacent to (e.g., pass over, between, near, etc.) the electrodes (such as electrodes 106 or 406A/406B). The electrodes may be connected to an AC voltage source and/or an amplifier (e.g., a multi-frequency lock-in amplifier), as described herein. A frequency dependent change in current may be exhibited as shown in the data provided on FIG. 1B. The frequency dependent change in current may be based on the amount, size, and/or type of biomarker coupled to the beads, for example. The amplitude of the current peak (e.g., in different frequencies) may depend on bead size, conductivity, and/or dielectric permittivity on the bead surface.

It may be difficult to distinguish one or more bead types from one other. For example, it may be difficult to distinguish one or more bead types from one other using single and/or dual frequency analysis (e.g., using single and/or dual frequency analysis alone), as shown in the scatter plot for voltage peak intensity at 600 kHz, 20 MHz, and 14 MHz on FIGS. 7A, 7B and FIGS. 8A, 8B.

Figure 8B:
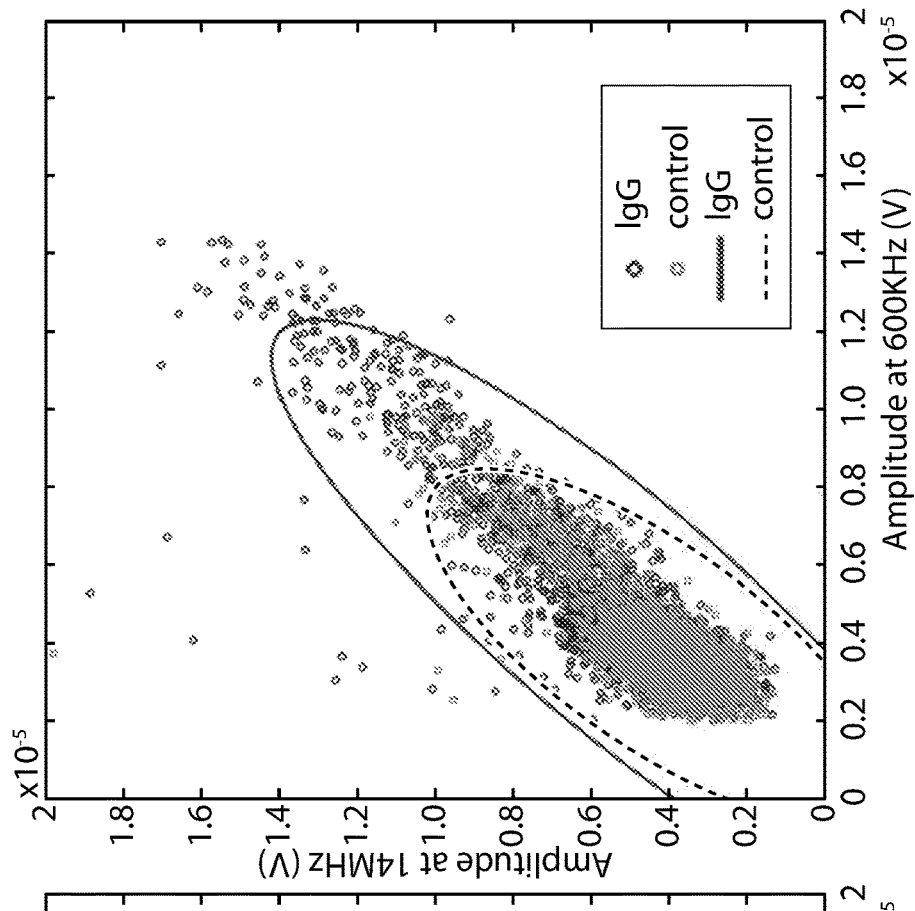
FIGS. 8A, 8B show additional example scatter plots for voltage peak intensities at 600 kHz, 20 MHz, and 14 MHz.
Figure 8A:
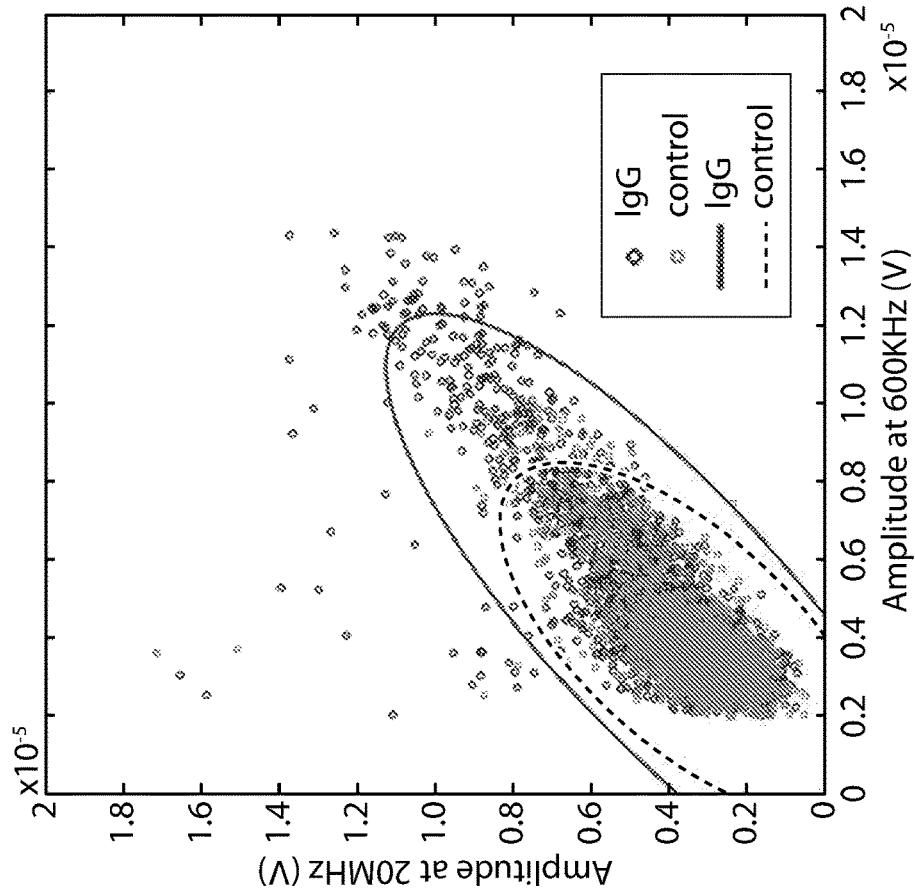
Figure 8C:
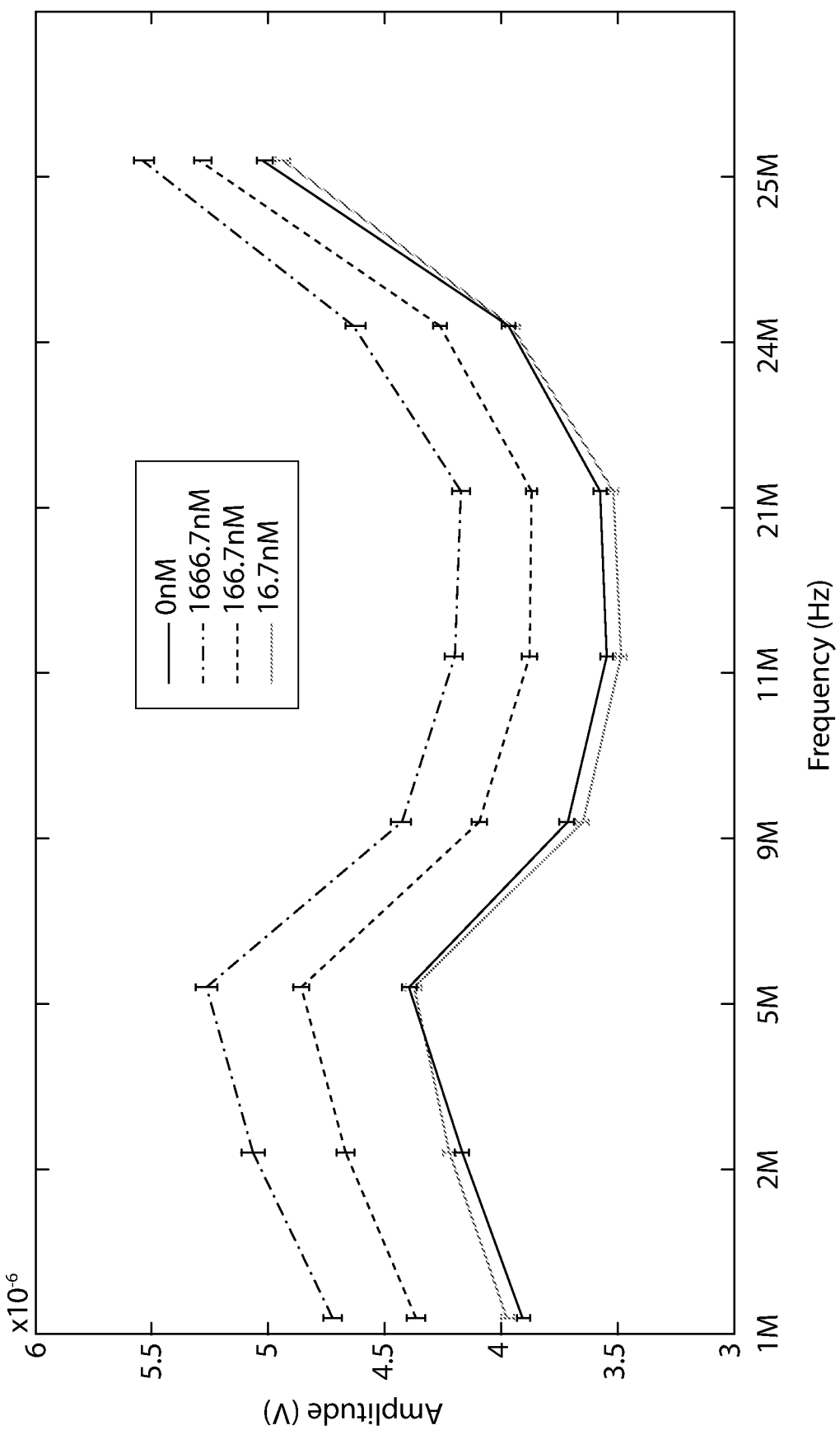
FIG. 8C shows another example plot of amplitudes based on a frequency for a plurality of concentrations.

Amplitudes resulting from the frequencies (e.g., the eight frequencies) may be averaged. For example, amplitudes resulting from the frequencies may be averaged (e.g., independently averaged) in two or more frequencies. When averaging amplitudes in two or more frequencies, there may be an amplitude drop from high concentration to low concentration. The amplitude drop may result from the amount of protein that may bind to the beads (as shown on FIG. 7C and FIG. 8C). For example, when the concentration is lower than 150 nM, differences in amplitude (e.g., average amplitude) may be difficult to observe. The differences in amplitude may be difficult to observe due to the size of the amplitudes (e.g., the small size of the amplitudes). The use of more than one (e.g., eight) frequencies and/or the use of machine learning techniques may assist in bead differentiation. For example, the use of eight frequencies and/or machine learning techniques may allow target IgG/IgA quantification (e.g., at tens of nanomolar) to be performed.

As described herein, machine learning techniques may assist in bead differentiation. To assist in bead differentiation, the machine learning model (e.g., the SVM model) may be trained with one or more types of data. For example, the machine learning model (e.g., the SVM model) may be trained with intensity (e.g., peak intensity) data. For example, the SVM model may be trained with intensity (e.g., peak intensity) data from IgG/IgA positive and IgG/IgA negative samples. The machine learning model may be trained with intensity (e.g., peak intensity) data at one or more (e.g., eight) frequencies. The machine learning model may test samples and/or determine algorithm classification accuracy for IgG/IgA positive and IgG/IgA negative beads. For example, as the concentration of target IgG/IgA in a biofluid (e.g., saliva) decreases, SVM classification accuracy may decrease. The classification accuracy may be used as a metric to quantify IgG/IgA levels. As described herein, a biomarker quantification score may be defined (e.g., formulated). The biomarker quantification score may be defined as (SVM Accuracy-50)/50. The biomarker quantification score may provide a self-calibrated method of quantifying biomarker levels.

Figure 9A:
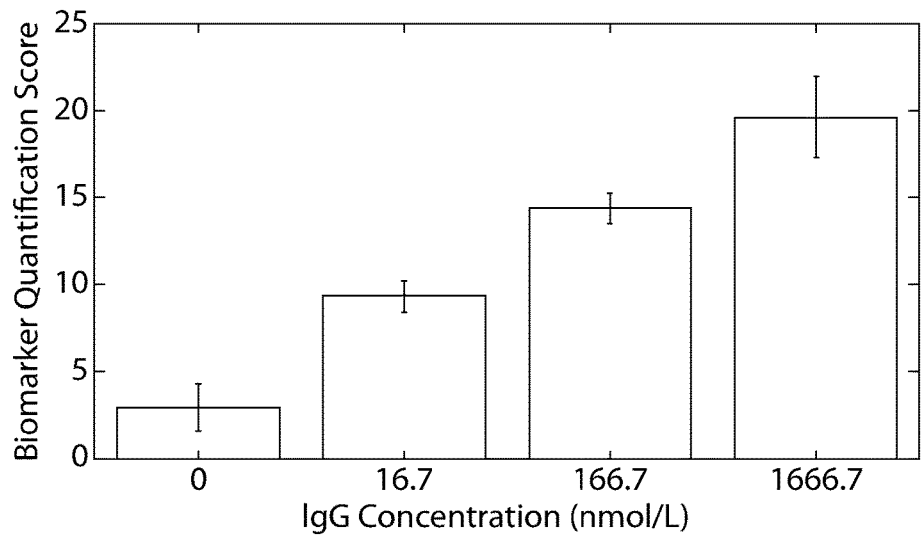
FIGS. 9A-9C show example plots of biomarker quantification scores.
Figure 9B:
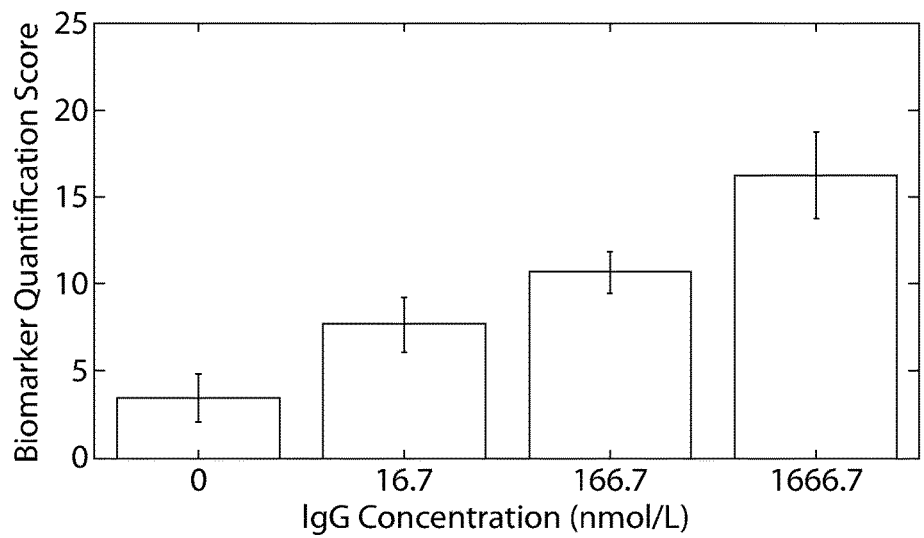
Figure 9C:
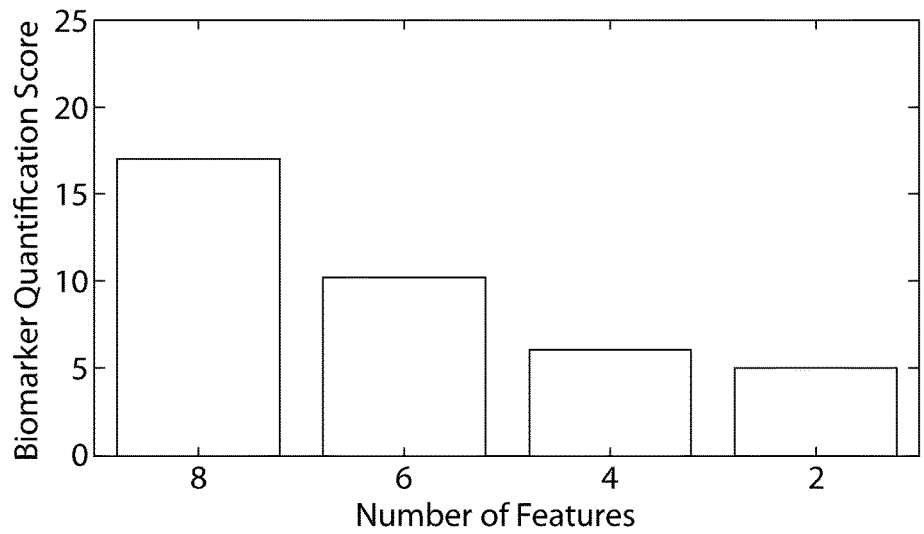

Biomarkers (e.g., biomarkers of interest) may be determined (e.g., scored). For example, biomarkers (e.g., biomarkers of interest) may be quantitatively determined (e.g., scored). FIGS. 9A, 9B show example biomarker scores (e.g., quantification scores) for dynamic ranges of 3 orders of magnitude and a repeatable detection limit (performed in triplicate) of 16.67 nM. In examples, the higher the quantification score the higher the accuracy of the classifier may be in differentiating between beads that have captured target protein and those that have not, which may correlate to a higher concentration of target protein biomarker in the test sample. FIG. 9C shows an example score increase with more frequencies involved in analysis. Such score increases as a result of more frequencies being involved reflects an improvement of the detection limit based on the number of frequencies being involved in analysis.

Data (e.g., experimental results/data) may show that through the combination of multi-frequency microfluidic impedance cytometry and supervised machine learning, biomarkers (e.g., immunoglobulins G and immunoglobulins A) in a biofluid (such as saliva) may be qualified. For example, biomarkers may be qualified within a time period, such as within two minutes. Although the disclosure describes IgG/IgA as example biomarkers for testing in the example saliva biofluid, it should be understood that the biomarkers and/or biofluids described in the disclosure are for illustration only and are non-limiting. The method can be performed using a wide variety of biomarkers (e.g., proteins) in a wide variety of biofluids. For example, the concepts described herein may be used to quantify one or more biomarker levels in complex samples, such as saliva, blood, urine, as well as others. Further, the features described herein are not limited nanoMolar computations and may be extended to other computations, such as picoMolar computations.

Figure 10:
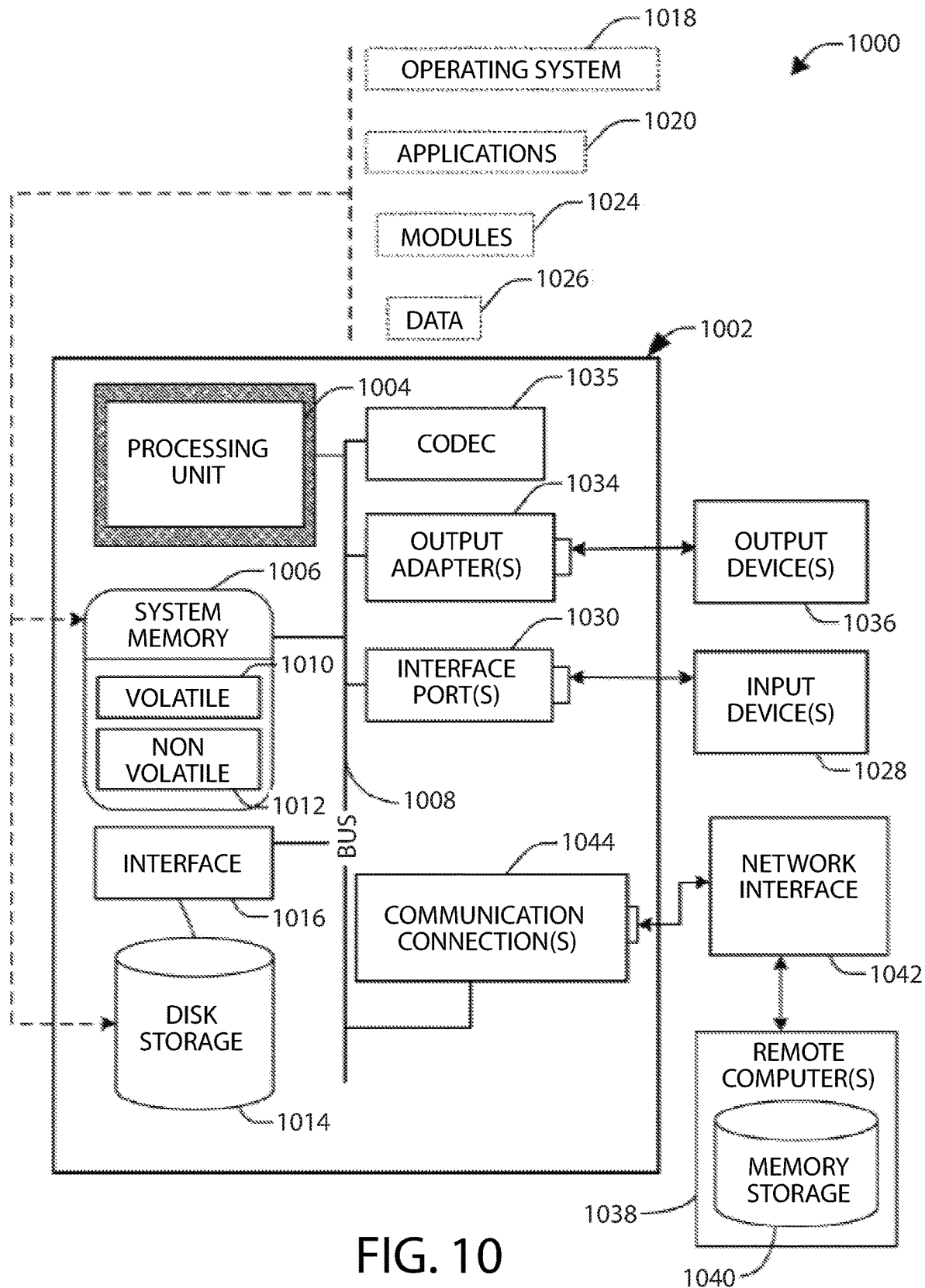
FIG. 10 shows an example environment for implementing various aspects of the subject matter described herein.

The systems and processes described herein can be embodied within hardware, such as the example hardware shown on FIG. 10. The hardware may include an integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

With reference to FIG. 10, an example environment 1000 for implementing various aspects of the claimed subject matter includes a computer 1002. The computer 1002 may include a processing unit 1004, a system memory 1006, a codec 1035, and/or a system bus 1008. The system bus 1008 may couple system components including, but not limited to, the system memory 1006 to the processing unit 1004. The processing unit 1004 can be any of various available processors. Dual microprocessors and other multiprocessor architectures also can be employed as the processing unit 1004.

The system bus 1008 may be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1006 may include volatile memory 1010 and/or non-volatile memory 1012, which may employ one or more of the disclosed memory architectures. The basic input/output system (BIOS), containing the basic routines to transfer information between elements within the computer 1002 (such as during start-up) may be stored in non-volatile memory 1012. Codec 1035 may include one or more of an encoder or decoder, wherein the encoder or decoder may consist of hardware, software, or a combination of hardware and software. Codec 1035 may be a separate component, or codec 1035 may be contained within non-volatile memory 1012.

Non-volatile memory 1012 may include read only memory (ROM), programmable ROM (PROM), electrically programmable ROM (EPROM), electrically erasable programmable ROM (EEPROM), Flash memory, 3D Flash memory, and/or resistive memory such as resistive random-access memory (RRAM). Non-volatile memory 1012 may employ one or more of the disclosed memory devices. Non-volatile memory 1012 may be computer memory (e.g., physically integrated with computer 1002 or a mainboard thereof), and/or removable memory. Examples of removable memory may include a secure digital (SD) card, a compact Flash (CF) card, a universal serial bus (USB) memory stick, or the like. Volatile memory 1010 may include random access memory (RAM), which may act as external cache memory, and/or may employ one or more disclosed memory devices. RAM may be available in many forms such as static RAM (SRAM), dynamic RAM (DRAM), synchronous DRAM (SDRAM), double data rate SDRAM (DDR SDRAM), enhanced SDRAM (ESDRAM), and so forth.

Computer 1002 may include removable/non-removable, volatile/non-volatile computer storage medium. FIG. 10 illustrates, for example, disk storage 1014. Disk storage 1014 may include, but is not limited to, devices such as a magnetic disk drive, solid state disk (SSD), flash memory card, or memory stick. Disk storage 1014 may include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1014 to the system bus 1008, a removable or non-removable interface may be used, such as interface 1016. Storage devices 1014 may store information related to a user. Such information may be stored at or provided to a server or to an application running on a user device. A user may be notified (e.g., by way of output device(s) 1036) of the types of information that may be stored to disk storage 1014 and/or transmitted to the server or application. The user may be provided the opportunity to opt-in or opt-out of having such information collected or shared with the server or application (e.g., by way of input from input device(s) 1028).

FIG. 10 describes software that may act as an intermediary between users and the basic computer resources described in the operating environment 1000. Such software may include an operating system 1018. Operating system 1018, which may be stored on disk storage 1014, may act to control and/or allocate resources of the computer system 1002. Applications 1020 may take advantage of the management of resources by operating system 1018 through program modules 1024, and program data 1026, such as the boot/shutdown transaction table and the like, stored in system memory 1006 and/or on disk storage 1014. The claimed subject matter may be implemented with various operating systems or combinations of operating systems.

A user may enter commands and/or information into the computer 1002 through input device(s) 1028. Input devices 1028 may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices may connect to the processing unit 1004 through the system bus 1008 via interface port(s) 1030. Interface port(s) 1030 may include, for example, a serial port, a parallel port, a game port, and/or a universal serial bus (USB). Output device(s) 1036 may use some of the same type of ports as input device(s) 1028. For example, a USB port may be used to provide input to computer 1002 and/or to output information from computer 1002 to an output device 1036. Output adapter 1034 is provided to illustrate that there may be some output devices 1036 like monitors, speakers, and printers, among other output devices 1036, which require special adapters. The output adapters 1034 may include video and sound cards that provide a means of connection between the output device 1036 and the system bus 1008. It should be noted that other devices or systems of devices provide both input and output capabilities such as remote computer(s) 1038.

Computer 1002 may operate in a networked environment using logical connections to one or more remote computers, such as remote computer(s) 1038. The remote computer(s) 1038 may include be a personal computer, a server, a router, a network PC, a workstation, a microprocessor-based appliance, a peer device, a smart phone, a tablet, or other network node, and may include many of the elements described relative to computer 1002. For purposes of brevity, only a memory storage device 1040 is illustrated with remote computer(s) 1038. Remote computer(s) 1038 is logically connected to computer 1002 through a network interface 1042 and connected via communication connection(s) 1044. Network interface 1042 may encompass wire or wireless communication networks such as local-area networks (LAN) and wide-area networks (WAN) and cellular networks. LAN technologies may include Fiber Distributed Data Interface (FDDI), Copper Distributed Data Interface (CDDI), Ethernet, Token Ring and the like. WAN technologies may include, but are not limited to, point-to-point links, circuit switching networks like Integrated Services Digital Networks (ISDN) and variations thereon, packet switching networks, and Digital Subscriber Lines (DSL).

Communication connection(s) 1044 may refer to the hardware/software employed to connect the network interface 1042 to the bus 1008. While communication connection 1044 is shown for illustrative clarity inside computer 1002, it may be external to computer 1002. The hardware/software necessary for connection to the network interface 1042 may include, for example, internal and external technologies such as, modems including regular telephone grade modems, cable modems and DSL modems, ISDN adapters, and wired and wireless Ethernet cards, hubs, and/or routers.

Figure 11:
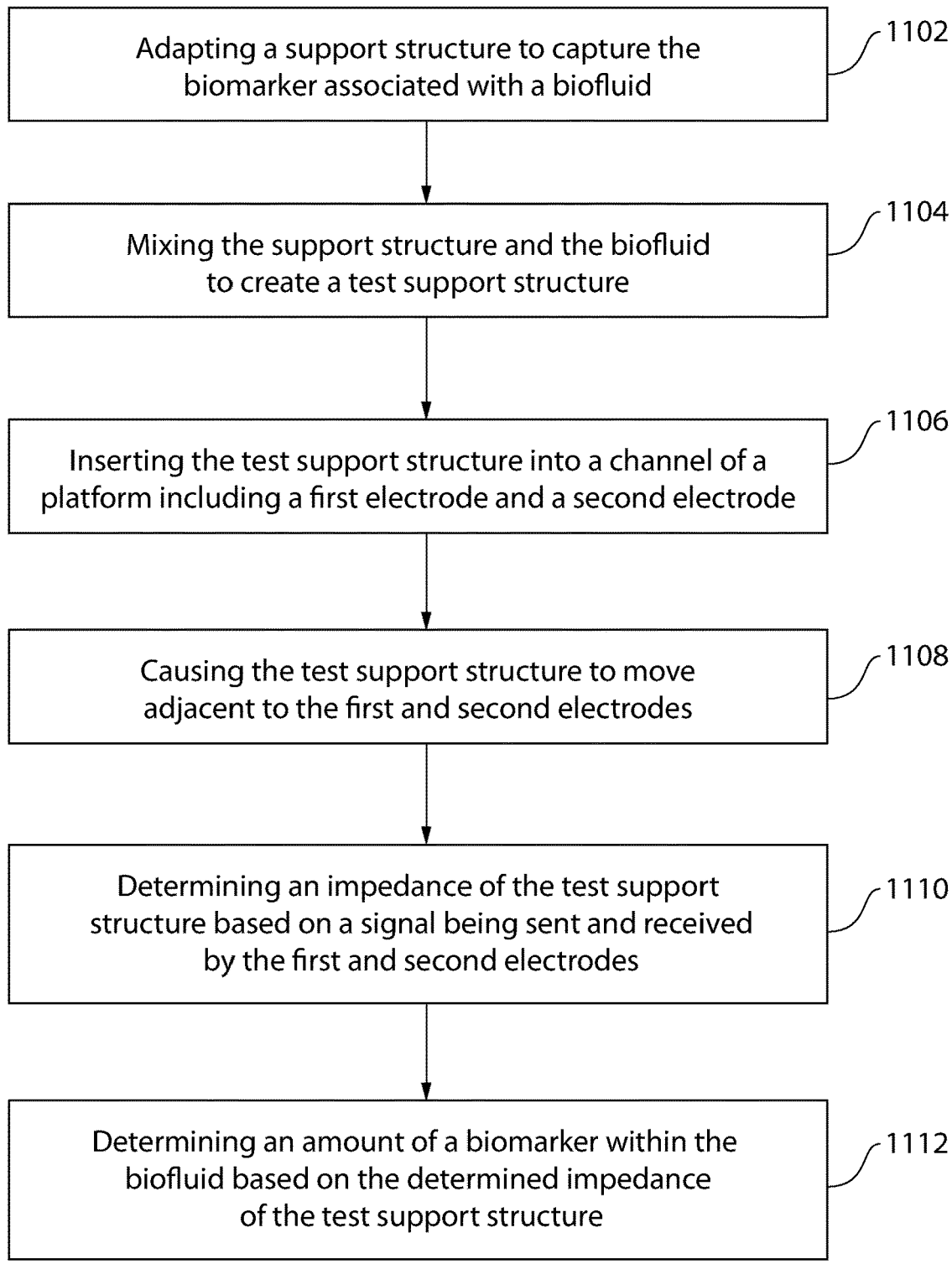
FIG. 11 shows an example process for for quantifying one or more biomarkers.

| FIG. 11 is an example method 1100 for quantifying one or more biomarkers. The biomarker may be a protein, such as an immunoglobin, as described herein. At 1102, a support structure is adapted. The support structure may be a bead, such as a magnetic bead, although the support structure may be one or more other form factors. The support structure may be adapted to capture a biomarker, such as a protein. The biomarker may be associated with a biofluid. For example, the biofluid may comprise the biomarker. The biofluid may be saliva, blood, urine, or another fluid. The support structure may be adapted via a coating, as described herein. Coating a bead may permit (e.g., assist) the beads to couple to one or more biomarkers. As an example, 2.8 μm beads (e.g., paramagnetic Dynal beads) may be coated with a coating material. The coating material may be anti-mouse IgG antibodies. The beads may be coated with anti-mouse IgG antibodies so that the beads may capture the mouse IgG in the biofluid (e.g., a saliva sample).

At 1104, the support structure may be mixed with the biofluid. The support structure and biofluid (e.g., the biomarker in the biofluid) may be mixed via a mixing device, such as mixing device 602 shown on FIG. 6A. Mixing device 602 may include a channel, such as channel 654. The mixing device may also, or alternatively, performing a filtering (e.g., a filtering of large particles). A channel may be used (e.g., used exclusively) for mixing or the channel may be used for filtering. In other examples, a channel (e.g., the same channel) may be used for mixing and filtering. The support structure (e.g., the beads mixed with the spiked mouse IgG) may be rotated. For example, the beads mixed with the spiked mouse IgG may be rotated on mixing device 602 (e.g., for 2 minutes).

For IgA, biofluid (e.g., saliva) samples may be spiked with human IgA. For example, biofluid (e.g., saliva) samples may be spiked with human IgA at a concentration of 8.4 µM. Support structures (e.g., 2.8 µm tosylactivated beads) may be coated with antibodies (such as anti IgA antibodies), for example, to capture the biomarker (e.g., human IgA) in the biofluid (e.g., saliva) sample. The beads may be couple with a biomarker, such as a protein (e.g., human IgA). To couple with the biomarker (e.g., IgA), the support structure may be mixed with human IgA spiked biofluid (e.g., saliva) samples in the channel and/or rotated. The resultant mix of the support structure and the biofluid (e.g., the biomarker found in the biofluid) may be referred to as a test support structure.

The test support structure may be inserted in a biochip, such as biochip 102, 1106. The test support structure may be inserted into the biochip in one of various ways, such as via injecting the test support structure into the biochip. The test support structure may be inserted into a channel of the biochip. The channel may pass adjacent to (e.g., through, between, etc.) one or more electrodes, such as a first electrode and a second electrode, that are positioned on the biochip.

At 1108, the test support structure moves adjacent to one or more of the electrodes, for example, via a channel. The test support structure may be caused to move adjacent to one or more of the electrodes via a pressure, a pumping mechanism, etc. One or more of the electrodes may send a signal and one or more of the electrodes may receive a signal. The one or more electrodes that receive the signal may determine an impedance value, at 1110. The impedance value may relate to the test support structure.

The impedance value may be based on the amount, type, weight, etc. of biomarker. For example, the impedance value may be based on the amount, type, weight, etc. that is coupled to the test support structure. At 1112, a quantification of the biomarker may be determined. The quantification of the biomarker may be determined via an evaluation of one or more frequencies, as described herein. Also, or alternatively, the quantification of the biomarker may be determined via machine learning techniques, such as SVM machine learning techniques.

Statements of the Disclosure include:

Statement 1: A method for identifying the presence of a biomarker in a biological sample, comprising: functionalizing a solid support to increase its affinity for a biomarker associated with a disease, disorder or condition; mixing, the functionalized solid support and a biological sample to form a test sample; providing a platform comprising at least one channel, a first electrode for sending a signal and a second electrode for receiving the signal; inserting the test sample into a channel of the platform; calculating an impedance of the test sample based on the signal sent by the first electrode and received by the second electrode when the test sample is located adjacent to the first and second electrodes; and identifying the presence of the biomarker associated with a disease, disorder or condition based on the calculated impedance of the test sample.

Statement 2: A method according to Statement 1, further comprising the step of quantifying the amount of biomarker in the test sample.

Statement 3: A method according to Statement 1 or Statement 2, further comprising the step of determining the risk associated with developing, a disease, disorder or condition based on the amount of biomarker in the test sample.

Statement 4: A method according to Statements 1-3, wherein the solid support comprises an inert material.

Statement 5: A method according to Statements 1-4, wherein the solid support is selected from: a bead; a particle; a film; a slide; a zeolite; and a hydrogel.

Statement 6: A method according Statements 1-5, wherein the platform is a micro-fluidic biochip, wherein the channel, the first electrode, and the second electrode are formed on the micro-fluidic biochip.

Statement 7: A method according to Statements 1-6, wherein the biomarker is selected from: APP; Cystatin A; Cystatin B; Cystatin C; Cystatin E/M; EMMPRIN; Fetuin B; HAI-1; HAI-2; HE4/WFDC2; Latexin; Lipocalin-1; Lipocalin-2/NGAL; RECK; Serpin A5; Serpin A8/AGT; Serpin A9/Centerin; Serpin A12; Serpin B5/Maspin; Serpin B6; Serpin B8; Serpin E1/PAI-1; Serpin F1/PEDF; Testican 1/SPOCK1; Testican 2/SPOCK2; TFPI; TFPI-2; TIMP-1; TIMP-2; TIMP-3; TIMP-4; Trappin-2/Elafin; Cathepsin B; Cathepsin C/DPPI; Cathepsin D; Cathepsin E; Cathepsin L; Cathepsin S; Cathepsin V; Cathepsin X/Z/P; DPPIV/CD26; Kallikrein 3/PSA; Kallikrein 5; Kallikrein 6; Kallikrein 7; Kallikrein 10; Kallikrein 11; Kallikrein 13; MMP-1; MMP-2; MMP-3; MMP-7; MMP-8; MMP-9; MMP-10; MMP-12; MMP-13; Neprilysin/CD10; Presenilin-1; Proprotein Convertase 9; Proteinase 3; uPA/Urokinase; ADAM8; ADAM9; ADAMTS1; ADAMTS13; Cathepsin A; ADAMTS1; Bcl-2; Carbonic Anhydrase IX; Cited-2; COX-2; Cytochrome c; Dkk-4; FABP1/L-FABP; HIF-1 alpha; HIF-2 alpha; Phospho-HSP27 (S78/S82); HSP60; HSP70; IDO; Phospho-JNK Pan (T183/Y185); NFkappaB1; p21/CIP1; p27/Kip1; Phospho-p38 alpha (T180/Y182); Phospho-p53 (S46); PON1; PON2; PON3; Thioredoxin-1; SIRT2; SOD2; Adiponectin/Acrp30; Angiogenin; Angiopoietin-1; Angiopoietin-2; Apolipoprotein A1; BAFF/BLyS/TNFSF13B; BDNF; CD14; CD30; CD31/PECAM-1; CD40 Ligand/TNFSF5; Chitinase 3-like; Complement Component C5/C5a; Complement Factor D; C-Reactive Protein/CRP; Cripto-1; Cystatin C; Dkk-1; DPPIV/CD26; EGF; CXCL5/ENA-78; Endoglin/CD105; Fas Ligand; FGF basic; KGF/FGF-7; FGF-19; Flt-3 Ligand; G-CSF; GDF-15; GM-CSF; CXCL1/GRO alpha; Growth Hormone (GH); HGF; ICAM-1/CD54; IFN-gamma; IGFBP-2; IGFBP-3; IL-1 alpha/IL-1F1; IL-1 beta/IL-1F2; IL-1ra/IL-1F3; IL-2; IL-3; IL-4; IL-5; IL-6; IL-8; IL-10; IL-11; IL-12 p70; IL-13; IL-15; IL-16; IL-17A; IL-18 BPa; IL-19; IL-22; IL-23; IL-24; IL-27; IL-31; IL-32 alpha/beta/gamm; IL-33; IL-34; CXCL10/IP-10; CXCL11/I-TAC; Kallikrein 3/PSA; Leptin; LIF; Lipocalin-2/NGAL; CCL2/MCP-1; CCL7/MCP-3; M-CSF; MIF; CXCL9/MIG; CCL3/CCL4 MIP-1 alpha/beta; CCL20/MIP-3 alpha; CCL19/MIP-3 beta; MMP-9; Myeloperoxidase; Osteopontin (OPN); PDGF-AA; PDGF-AB/BB; Pentraxin 3/TSF-14; CXCL4/PF4; RAGE; CCL5/RANTES; RBP; Relaxin-2; Resistin; CXCL12/SDF-1 alpha; Serpin E1/PAI-1. SHBG; ST2/IL1 R4; CCL17/TARC; TFF3; TfR; TGF-alpha; Thrombospondin-1; TIM-1; TNF-alpha; uPAR; VCAM-1; VEGF; Vitamin D BP; and a combination of two or more thereof.

Statement 8: A method according to Statements 1-7, wherein functionalizing (or adapting) the solid support to increase its affinity for a biomarker associated with a disease, disorder or condition comprises covalent coupling, chemical adsorption, physical adsorption or a combination thereof.

Statement 9: A method according to Statements 1-8, wherein the mixing comprises (1) a mixing of the solid support and the biological sample; and (2) filtering particles from the biological sample.

Statement 10: A method according to Statements 1-9, wherein the disease, disorder or condition is selected from: an inflammatory condition; a bacterial infection; a viral infection; a fungal infection; a cancer; a traumatic injury; and combination of two or more thereof.

Statement 11: A method according to Statements 1-10, wherein the disease, disorder or condition is a disease, disorder or condition of the oral cavity.

Statement 12: A method according to Statement 11, wherein the disease, disorder or condition of the oral cavity is selected from: gingivitis; periodontitis; a herpes simplex virus; candidiasis; a canker sore; caries; halitosis; xerostomia; and a combination of two or more thereof.

Statement 13: A method according to Statements 1-12, wherein the presence of the biomarker is quantified in from about 30 seconds to about 30 minutes, optionally from about 60 seconds to about 15 minutes, optionally from about 90 seconds to about 10 minutes, further optionally from about 2 minutes to about 5 minutes.

Statement 14: A method according to Statements 1-13, wherein the presence of the biomarker is quantified in less than about 5 minutes, optionally less than about 4 minutes, optionally less than about 3 minutes, optionally about 2 minutes, further optionally less than about 2 minutes.

Statement 15: A method according to Statements 3-14, wherein the presence of, or the risk associated with developing, a disease, disorder or condition is determined in from about 30 seconds to about 30 minutes, optionally from about 60 seconds to about 15 minutes, optionally from about 90 seconds to about 10 minutes, further optionally from about 2 minutes to about 5 minutes.

Statement 16: A method according to Statements 3-15, wherein the presence of, or the risk associated with developing, a disease, disorder or condition is determined in less than about 5 minutes, optionally less than about 4 minutes, optionally less than about 3 minutes, optionally about 2 minutes, further optionally less than about 2 minutes.

Statement 17: A method according to Statements 1-16, wherein the biological sample comprises saliva, blood, urine, sweat, exhaled breath condensate, a tissue, or a combination thereof.

Statement 18: A method according to Statements 1-17, wherein the biological sample comprises saliva.

Statement 19: A method according to Statements 1-18, wherein the biological sample has, or is configured to have, a viscosity at about 20° C., of from about 1 cP to about 100 cP, optionally from about 1 cP to about 50 cP, or about 1 cP to about 25 cP, or about 1 cP to about 10 cP, or about 1 cP to about 5 cP, or about 1 cP to about 3 cP, or about 1 cP to about 2 cP.

Statement 20: A method according to Statements 1-19, wherein the test sample has a viscosity at about 20° C., of from about 1 cP to about 100 cP, optionally from about 1 cP to about 50 cP, or about 1 cP to about 25 cP, or about 1 cP to about 10 cP, or about 1 cP to about 5 cP, or about 1 cP to about 3 cP, or about 1 cP to about 2 cP.

Statement 21: A method according to Statements 1-20, wherein the channel is substantially free of structure(s) that adversely impede(s) the flow of the test sample.

Statement 22: A biochip comprising: a channel comprising an inlet for receiving a test sample, the test sample comprising a biological sample and a solid support having an increased affinity for a biomarker associated with a disease, disorder or condition; a first electrode and a second electrode each positioned adjacent to the channel, the first electrode being configured to send a signal and the second electrode being configured to receive the signal; and a processor configured to: calculate an impedance value of the test sample from the signal sent by the first electrode and received by the second electrode, when the test sample is located adjacent to the first electrode and the second electrode.

Statement 23: A biochip according to Statement 22, wherein the processor is further configured to quantify the amount of the biomarker associated with a disease, disorder or condition, based on the calculated impedance value of the test sample.

Statement 24: A biochip according to Statement 23, wherein the processor is further configured to determine the presence of, or the risk associated with developing, a disease, disorder or condition based on the amount of biomarker in the test sample.

Statement 25: A biochip according to Statements 22-24, wherein the solid support comprises an inert material.

Statement 26: A biochip according to Statements 22-25, wherein the solid support is selected from a bead; a particle; a film; a slide; a zeolite; and a hydrogel.

Statement 27: A biochip according to Statements 22-26, wherein the biomarker is selected from: APP; Cystatin A; Cystatin B; Cystatin C; Cystatin E/M; EMMPRIN; Fetuin B; HAI-1; HAI-2; HE4/WFDC2; Latexin; Lipocalin-1; Lipocalin-2/NGAL; RECK; Serpin A5; Serpin A8/AGT; Serpin A9/Centerin; Serpin A12; Serpin B5/Maspin; Serpin B6; Serpin B8; Serpin E1/PAI-1; Serpin F1/PEDF; Testican 1/SPOCK1; Testican 2/SPOCK2; TFPI; TFPI-2; TIMP-1; TIMP-2; TIMP-3; TIMP-4; Trappin-2/Elafin; Cathepsin B; Cathepsin C/DPPI; Cathepsin D; Cathepsin E; Cathepsin L; Cathepsin S; Cathepsin V; Cathepsin X/Z/P; DPPIV/CD26; Kallikrein 3/PSA; Kallikrein 5; Kallikrein 6; Kallikrein 7; Kallikrein 10; Kallikrein 11; Kallikrein 13; MMP-1; MMP-2; MMP-3; MMP-7; MMP-8; MMP-9; MMP-10; MMP-12; MMP-13; Neprilysin/CD10; Presenilin-1; Proprotein Convertase 9; Proteinase 3; uPA/Urokinase; ADAM8; ADAM9; ADAMTS1; ADAMTS13; Cathepsin A; ADAMTS1; Bcl-2; Carbonic Anhydrase IX; Cited-2; COX-2; Cytochrome c; Dkk-4; FABP1/L-FABP; HIF-1 alpha; HIF-2 alpha; Phospho-HSP27 (S78/S82); HSP60; HSP70; IDO; Phospho-JNK Pan (T183/Y185); NFkappaB1; p21/CIP1; p27/Kip1; Phospho-p38 alpha (T180/Y182); Phospho-p53 (S46); PON1; PON2; PON3; Thioredoxin-1; SIRT2; SOD2; Adiponectin/Acrp30; Angiogenin; Angiopoietin-1; Angiopoietin-2; Apolipoprotein A1; BAFF/BLyS/TNFSF13B; BDNF; CD14; CD30; CD31/PECAM-1; CD40 Ligand/TNFSF5; Chitinase 3-like; Complement Component C5/C5a; Complement Factor D; C-Reactive Protein/CRP; Cripto-1; Cystatin C; Dkk-1; DPPIV/CD26; EGF; CXCL5/ENA-78; Endoglin/CD105; Fas Ligand; FGF basic; KGF/FGF-7; FGF-19; Flt-3 Ligand; G-CSF; GDF-15; GM-CSF; CXCL1/GRO alpha; Growth Hormone (GH); HGF; ICAM-1/CD54; IFN-gamma; IGFBP-2; IGFBP-3; IL-1 alpha/IL-1F1; IL-1 beta/IL-1F2; IL-Ira/IL-1F3; IL-2; IL-3; IL-4; IL-5; IL-6; IL-8; IL-10. IL-11; IL-12 p70; IL-13. IL-15; IL-16; IL-17A; IL-18 BPa; IL-19; IL-22; IL-23; IL-24; IL-27; IL-31; IL-32 alpha/beta/gamm; IL-33; IL-34; CXCL10/IP-10; CXCL11/I-TAC; Kallikrein 3/PSA; Leptin; LIF; Lipocalin-2/NGAL; CCL2/MCP-1; CCL7/MCP-3; M-CSF; MIF; CXCL9/MIG; CCL3/

CCL4 MIP-1 alpha/beta; CCL20/MIP-3 alpha; CCL19/ MIP-3 beta; MMP-9; Myeloperoxidase; Osteopontin (OPN); PDGF-AA; PDGF-AB/BB; Pentraxin 3/TSF-14; CXCL4/PF4; RAGE; CCL5/RANTES; RBP; Relaxin-2; Resistin; CXCL12/SDF-1 alpha; Serpin E1/PAI-1; SHBG; ST2/IL1 R4; CCL17/TARC; TFF3; TfR; TGF-alpha; Thrombospondin-1; TIM-1; TNF-alpha; uPAR; VCAM-1; VEGF; Vitamin D BP; and a combination of two or more thereof.

Statement 28: A biochip according to Statements 22-27, wherein the disease, disorder or condition is selected from: an inflammatory condition; a bacterial infection; a viral infection; a fungal infection; a cancer; a traumatic injury; and combination of two or more thereof.

Statement 29: A biochip according to Statements 22-28, wherein the disease, disorder or condition is a disease, disorder or condition of the oral cavity.

Statement 30: A biochip according to Statement 29, wherein the disease, disorder or condition of the oral cavity is selected from: gingivitis; periodontitis; a herpes simplex virus; candidiasis; a canker sore; caries; halitosis; xerostomia; and a combination of two or more thereof.

Statement 31: A biochip according to Statements 23-30, wherein the amount of the biomarker can be quantified in from about 30 seconds to about 30 minutes, optionally from about 60 seconds to about 15 minutes, optionally from about 90 seconds to about 10 minutes, further optionally from about 2 minutes to about 5 minutes.

Statement 32: A biochip according to Statements 23-31, wherein the amount of the biomarker can be quantified in less than about 5 minutes, optionally less than about 4 minutes, optionally less than about 3 minutes, optionally about 2 minutes, further optionally less than about 2 minutes.

Statement 33: A biochip according to Statements 24-32, wherein the presence of, or the risk associated with developing, a disease, disorder or condition is determined in from about 30 seconds to about 30 minutes, optionally from about 60 seconds to about 15 minutes, optionally from about 90 seconds to about 10 minutes, further optionally from about 2 minutes to about 5 minutes.

Statement 34: A biochip according to Statements 24-33, wherein the presence of, or the risk associated with developing, a disease, disorder or condition is determined in less than about 5 minutes, optionally less than about 4 minutes, optionally less than about 3 minutes, optionally about 2 minutes, further optionally less than about 2 minutes.

Statement 35: A biochip according to Statements 22-34, wherein the biological sample comprises saliva, blood, urine, sweat, exhaled breath condensate, a tissue, or a combination thereof.

Statement 36: A biochip according to Statements 22-35, wherein the biological sample comprises saliva.

Statement 37: A biochip according to Statements 22-36, wherein the biological sample has, or is configured to have, a viscosity at about 20° C., of from about 1 cP to about 100 cP, optionally from about 1 cP to about 50 cP, or about 1 cP to about 25 cP, or about 1 cP to about 10 cP, or about 1 cP to about 5 cP, or about 1 cP to about 3 cP, or about 1 cP to about 2 cP.

Statement 38: A biochip according to Statements 22-37, wherein the test sample has a viscosity at about 20° C., of from about 1 cP to about 100 cP, optionally from about 1 cP to about 50 cP, or about 1 cP to about 25 cP, or about 1 cP to about 10 cP, or about 1 cP to about 5 cP, or about 1 cP to about 3 cP, or about 1 cP to about 2 cP.

Statement 39: A biochip according to Statements 22-38, wherein the test sample further comprises a buffer.

Statement 40: A system, comprising: a mixing device configured to mix a solid support and a biological sample to form a test sample; a biochip, comprising: a channel comprising an inlet for receiving the test sample; a first electrode and a second electrode positioned adjacent to the channel, the first electrode being configured to send a signal and the second electrode being configured to receive the signal; and a processor configured to: calculate an impedance value based on the signal being sent by the first electrode and being received by the second electrode when the test sample is located adjacent to the first and second electrodes; and quantify the amount of a biomarker associated with a disease, disorder or condition, based on the calculated impedance of the test sample.

Statement 41: A system of Statement 40, wherein the processor identifies the presence of a disease, disorder or condition based on the calculated amount of the biomarker.

Statement 42: A system according to Statement 40 or Statement 41, wherein the solid support comprises an inert material.

Statement 43: A system according to Statements 40-42, wherein the solid support is selected from: a bead; a particle; a film; a slide; a zeolite; and a hydrogel.

Statement 44: A system according to Statements 40-43, wherein the biomarker is selected from: APP; Cystatin A; Cystatin B; Cystatin C; Cystatin E/M; EMMPRIN; Fetuin B; HAI-1; HAI-2; HE4/WFDC2; Latexin; Lipocalin-1; Lipocalin-2/NGAL; RECK; Serpin A5; Serpin A8/AGT; Serpin A9/Centerin; Serpin A12; Serpin B5/Maspin; Serpin B6; Serpin B8; Serpin E1/PAI-1; Serpin F1/PEDF; Testican 1/SPOCK1; Testican 2/SPOCK2; TFPI; TFPI-2; TIMP-1; TIMP-2; TIMP-3; TIMP-4; Trappin-2/Elafin; Cathepsin B; Cathepsin C/DPPI; Cathepsin D; Cathepsin E; Cathepsin L; Cathepsin S; Cathepsin V; Cathepsin X/Z/P; DPPIV/CD26; Kallikrein 3/PSA; Kallikrein 5; Kallikrein 6; Kallikrein 7; Kallikrein 10; Kallikrein 11; Kallikrein 13; MMP-1; MMP-2; MMP-3; MMP-7; MMP-8; MMP-9; MMP-10; MMP-12; MMP-13; Neprilysin/CD10; Presenilin-1; Proprotein Convertase 9; Proteinase 3; uPA/Urokinase; ADAM8; ADAM9; ADAMTS1; ADAMTS13; Cathepsin A; ADAMTS1; Bcl-2; Carbonic Anhydrase IX; Cited-2; COX-2; Cytochrome c; Dkk-4; FABP1/L-FABP; HIF-1 alpha; HIF-2 alpha; Phospho-HSP27 (S78/S82); HSP60; HSP70; IDO; Phospho-JNK Pan (T183/Y185); NFkappaB1; p21/CIP1; p27/Kip1; Phospho-p38 alpha (T180/Y182); Phospho-p53 (S46); PON1; PON2; PON3; Thioredoxin-1; SIRT2; SOD2; Adiponectin/Acrp30; Angiogenin; Angiopoietin-1; Angiopoietin-2; Apolipoprotein A1; BAFF/BLyS/TNFSF13B; BDNF; CD14; CD30; CD31/PECAM-1; CD40 Ligand/TNFSF5; Chitinase 3-like; Complement Component C5/C5a; Complement Factor D; C-Reactive Protein/CRP; Cripto-1; Cystatin C; Dkk-1; DPPIV/CD26; EGF; CXCL5/ENA-78; Endoglin/CD105; Fas Ligand; FGF basic; KGF/FGF-7; FGF-19; Flt-3 Ligand; G-CSF; GDF-15; GM-CSF; CXCL1/GRO alpha; Growth Hormone (GH); HGF; ICAM-1/CD54; IFN-gamma; IGFBP-2; IGFBP-3; IL-1 alpha/IL-1F1; IL-1 beta/IL-1F2; IL-1ra/IL-1F3; IL-2; IL-3; IL-4; IL-5; IL-6; IL-8; IL-10; IL-11; IL-12 p70; IL-13; IL-15; IL-16; IL-17A; IL-18 BPa; IL-19; IL-22; IL-23; IL-24; IL-27; IL-31; IL-32 alpha/beta/gamm; IL-33; IL-34; CXCL10/IP-10; CXCL11/I-TAC; Kallikrein 3/PSA; Leptin; LIF; Lipocalin-2/NGAL; CCL2/MCP-1; CCL7/MCP-3; M-CSF; MIF; CXCL9/MIG; CCL3/CCL4 MIP-1 alpha/beta; CCL20/MIP-3 alpha; CCL19/MIP-3 beta; MMP-9; Myeloperoxidase; Osteopontin (OPN); PDGF-AA; PDGF-AB/BB; Pentraxin 3/TSF-14;

CXCL4/PF4; RAGE; CCL5/RANTES; RBP; Relaxin-2; Resistin; CXCL12/SDF-1 alpha; Serpin E1/PAI-1; SHBG; ST2/IL1 R4; CCL17/TARC; TFF3; TfR; TGF-alpha; Thrombospondin-1; TIM-1; TNF-alpha; uPAR; VCAM-1. VEGF; Vitamin D BP; and a combination of two or more thereof.

Statement 45: A system according to Statements 40-44, further comprising the step of functionalizing the solid support to increase its affinity for a biomarker associated with a disease, disorder or condition.

Statement 46: A system according to Statement 45, wherein the step of functionalizing the solid support to increase its affinity for a biomarker associated with a disease, disorder or condition comprises covalent coupling, chemical adsorption, physical adsorption or a combination thereof.

Statement 47: A system according to Statements 40-46, wherein the disease, disorder or condition is selected from: an inflammatory condition; a bacterial infection; a viral infection; a fungal infection; a cancer; a traumatic injury; and combination of two or more thereof.

Statement 48: A system according to Statements 40-47, wherein the disease, disorder or condition is a disease, disorder or condition of the oral cavity.

Statement 49: A system according to Statement 48, wherein the disease, disorder or condition of the oral cavity is selected from: gingivitis; periodontitis; a herpes simplex virus; candidiasis; a canker sore; caries; halitosis; xerostomia; and a combination of two or more thereof.

Statement 50: A system according to Statements 40-49, wherein an amount of the biomarker is quantified in from about 30 seconds to about 30 minutes, optionally from about 60 seconds to about 15 minutes, optionally from about 90 seconds to about 10 minutes, further optionally from about 2 minutes to about 5 minutes.

Statement 51: A system according to Statements 40-50, wherein an amount of the biomarker is quantified in less than about 5 minutes, optionally less than about 4 minutes, optionally less than about 3 minutes, optionally about 2 minutes, further optionally less than about 2 minutes.

Statement 52: A system according to Statements 41-51, wherein the presence of, or the risk associated with developing, a disease, disorder or condition is determined in from about 30 seconds to about 30 minutes, optionally from about 60 seconds to about 15 minutes, optionally from about 90 seconds to about 10 minutes, further optionally from about 2 minutes to about 5 minutes.

Statement 53: A system according to Statements 41-52, wherein the presence of, or the risk associated with developing, a disease, disorder or condition is determined in less than about 5 minutes, optionally less than about 4 minutes, optionally less than about 3 minutes, optionally about 2 minutes, further optionally less than about 2 minutes.

Statement 54: A system according to Statements 40-53, wherein the biological sample comprises saliva, blood, urine, sweat, exhaled breath condensate, a tissue, or a combination thereof.

Statement 55: A system according to Statements 40-54, wherein the biological sample comprises saliva.

Statement 56: A system according to Statements 40-55, wherein the biological sample has, or is configured to have, a viscosity at about 20° C., of from about 1 cP to about 100 cP, optionally from about 1 cP to about 50 cP, or about 1 cP to about 25 cP, or about 1 cP to about 10 cP, or about 1 cP to about 5 cP, or about 1 cP to about 3 cP, or about 1 cP to about 2 cP.

Statement 57: A system according to Statements 40-56, wherein the test sample has a viscosity at about 20° C., of from about 1 cP to about 100 cP, optionally from about 1 cP to about 50 cP, or about 1 cP to about 25 cP, or about 1 cP to about 10 cP, or about 1 cP to about 5 cP, or about 1 cP to about 3 cP, or about 1 cP to about 2 cP.

Statement 58: A method of treating a disease, disorder or condition in a mammalian subject, comprising: identifying the presence of a biomarker in a biological sample obtained from a mammalian subject, comprising: functionalizing a solid support to increase its affinity for a biomarker associated with a disease, disorder or condition; mixing, the functionalized solid support and a biological sample to form a test sample; providing a platform comprising at least one channel, a first electrode for sending a signal and a second electrode for receiving the signal; inserting the test sample into a channel of the platform; calculating an impedance of the test sample based on the signal sent by the first electrode and received by the second electrode when the test sample is located adjacent to the first and second electrodes; quantifying the presence of the biomarker associated with a disease, disorder or condition based on the impedance calculated from the test sample; determining the presence of, or the risk associated with developing, a disease, disorder or condition based on the amount of biomarker in the test sample; and administering a composition comprising an ingredient effective in treating or preventing the disease, disorder or condition to a mammalian subject in need thereof.

Statement 59: A method according to Statement 58, wherein aberrant levels of the biomarker indicate the presence of, or an elevated risk associated with developing, a disease, disorder or condition.

Statement 60: A method according to Statement 58 or Statement 59, wherein the method further comprises the step of obtaining a biological sample from a mammalian subject.

Statement 61: A method according to Statements 58-60, wherein the disease, disorder or condition is a disease, disorder or condition of the oral cavity.

Statement 62: A method according to Statement 61, wherein the ingredient effective in treating or preventing the disease, disorder or condition of the oral cavity is selected from a zinc ion source; a stannous ion source, arginine; a fluoride ion source; a peroxide source; an antibacterial agent (e.g. cetylpyridinium chloride); an anti-inflammatory agent; and a combination of two or more thereof.

Statement 63: A method for identifying a mammalian subject suffering from, or at risk for developing, a disease, disorder or condition, comprising: obtaining a biological sample from a mammalian subject; functionalizing a solid support to increase its affinity for a biomarker associated with a disease, disorder or condition; mixing, the functionalized solid support and the biological sample to form a test sample; providing a platform comprising at least one channel, a first electrode for sending a signal and a second electrode for receiving the signal; inserting the test sample into a channel of the platform; calculating an impedance of the test sample based on the signal being sent by the first electrode and being received by the second electrode when the test sample is located adjacent to the first and second electrodes; quantifying the presence of the biomarker associated with a disease, disorder or condition based on the calculated impedance of the test sample; wherein aberrant levels of the biomarker indicate the presence of, or an elevated risk associated with developing, a disease, disorder or condition.

Statement 64: A method according to Statements 58-63, wherein the biomarker is selected from: APP; Cystatin A; Cystatin B; Cystatin C; Cystatin E/M; EMMPRIN; Fetuin B; HAI-1; HAI-2; HE4/WFDC2; Latexin; Lipocalin-1; Lipocalin-2/NGAL; RECK; Serpin A5; Serpin A8/AGT; Serpin A9/Centerin; Serpin A12; Serpin B5/Maspin; Serpin B6; Serpin B8; Serpin E1/PAI-1; Serpin F1/PEDF; Testican 1/SPOCK1; Testican 2/SPOCK2; TFPI; TFPI-2; TIMP-1; TIMP-2; TIMP-3; TIMP-4; Trappin-2/Elafin; Cathepsin B; Cathepsin C/DPPI; Cathepsin D; Cathepsin E; Cathepsin L; Cathepsin S; Cathepsin V; Cathepsin X/Z/P; DPPIV/CD26; Kallikrein 3/PSA; Kallikrein 5; Kallikrein 6; Kallikrein 7; Kallikrein 10; Kallikrein 11; Kallikrein 13; MMP-1; MMP-2; MMP-3; MMP-7; MMP-8; MMP-9; MMP-10; MMP-12; MMP-13; Neprilysin/CD10; Presenilin-1; Proprotein Convertase 9; Proteinase 3; uPA/Urokinase; ADAM8; ADAM9; ADAMTS1; ADAMTS13; Cathepsin A; ADAMTS1; Bcl-2; Carbonic Anhydrase IX; Cited-2; COX-2; Cytochrome c; Dkk-4; FABP1/L-FABP; HIF-1 alpha; HIF-2 alpha; Phospho-HSP27 (S78/S82); HSP60; HSP70; IDO; Phospho-JNK Pan (T183/Y185); NFkappaB1; p21/CIP1; p27/Kip1; Phospho-p38 alpha (T180/Y182); Phospho-p53 (S46); PON1; PON2; PON3; Thioredoxin-1; SIRT2; SOD2; Adiponectin/Acrp30; Angiogenin; Angiopoietin-1; Angiopoietin-2; Apolipoprotein A1; BAFF/BLyS/TNFSF13B; BDNF; CD14; CD30; CD31/PECAM-1; CD40 Ligand/TNFSF5; Chitinase 3-like; Complement Component C5/C5a; Complement Factor D; C-Reactive Protein/CRP; Cripto-1; Cystatin C; Dkk-1; DPPIV/CD26; EGF; CXCL5/ENA-78; Endoglin/CD105; Fas Ligand; FGF basic; KGF/FGF-7; FGF-19; Flt-3 Ligand; G-CSF; GDF-15; GM-CSF; CXCL1/GRO alpha; Growth Hormone (GH); HGF; ICAM-1/CD54; IFN-gamma; IGFBP-2; IGFBP-3; IL-1 alpha/IL-1F1; IL-1 beta/IL-1F2; IL-Ira/IL-1F3; IL-2; IL-3; IL-4; IL-5; IL-6; IL-8; IL-10; IL-11; IL-12 p70; IL-13; IL-15; IL-16; IL-17A; IL-18 BPa; IL-19; IL-22; IL-23; IL-24; IL-27; IL-31; IL-32 alpha/beta/gamm; IL-33; IL-34; CXCL10/IP-10; CXCL11/I-TAC; Kallikrein 3/PSA; Leptin; LIF; Lipocalin-2/NGAL; CCL2/MCP-1; CCL7/MCP-3; M-CSF; MIF; CXCL9/MIG; CCL3/CCL4 MIP-1 alpha/beta; CCL20/MIP-3 alpha; CCL19/MIP-3 beta; MMP-9; Myeloperoxidase; Osteopontin (OPN); PDGF-AA; PDGF-AB/BB; Pentraxin 3/TSF-14; CXCL4/PF4; RAGE; CCL5/RANTES; RBP; Relaxin-2; Resistin; CXCL12/SDF-1 alpha; Serpin E1/PAI-1; SHBG; ST2/IL1 R4; CCL17/TARC; TFF3; TfR; TGF-alpha; Thrombospondin-1; TIM-1; TNF-alpha; uPAR; VCAM-1; VEGF; Vitamin D BP; and a combination of two or more thereof.

Statement 65: A method according to Statements 58-64, wherein the biological sample comprises saliva, blood, urine, sweat, exhaled breath condensate, a tissue, or a combination thereof.

Statement 66: A method according to Statements 58-65, wherein the biological sample comprises saliva.

Statement 67: A method according to Statements 58-66, wherein the biological sample has, or is configured to have, a viscosity at about 20° C., of from about 1 cP to about 100 cP, optionally from about 1 cP to about 50 cP, or about 1 cP to about 25 cP, or about 1 cP to about 10 cP, or about 1 cP to about 5 cP, or about 1 cP to about 3 cP, or about 1 cP to about 2 cP.

Statement 68: A method according to Statements 58-67, wherein the test sample has a viscosity at about 20° C., of from about 1 cP to about 100 cP, optionally from about 1 cP to about 50 cP, or about 1 cP to about 25 cP, or about 1 cP to about 10 cP, or about 1 cP to about 5 cP, or about 1 cP to about 3 cP, or about 1 cP to about 2 cP.

Statement 69: A method according to Statements 1-21 and/or 58-68, wherein multi-channel impedance is used to calculate the impedance of the test sample.

Statement 70: A method according to Statement 69, wherein multi-channel impedance is used to distinguish between a solid support bound to a biomarker and a solid support without a biomarker bound thereto.

Statement 71: A biochip according to Statements 22-39, wherein the biochip comprises a plurality of channels.

Statement 72: A biochip according to Statement 71, wherein multi-channel impedance is used to calculate the impedance of the test sample.

Statement 73: A biochip according to Statement 72, wherein multi-channel impedance is used to distinguish between a solid support bound to a biomarker and a solid support without a biomarker bound thereto.

Statement 74: A system according to Statements 40-57, wherein the biochip comprises a plurality of channels.

Statement 75: A system according to Statement 74, wherein multi-channel impedance is used to calculate the impedance of the test sample.

Statement 76: A system according to Statement 75, wherein multi-channel impedance is used to distinguish between a solid support bound to a biomarker and a solid support without a biomarker bound thereto.

While the present invention has been described with respect to specific examples including presently preferred modes of carrying out the invention, those skilled in the art will appreciate that there are numerous variations and permutations of the above-described systems and techniques. It is to be understood that other embodiments may be utilized and structural and functional modifications may be made without departing from the scope of the present invention. Thus, the spirit and scope of the present invention should be construed broadly as set forth in the appended claims.

What is claimed is:

1. A method for identifying the presence of a biomarker in a biological sample obtained from a mammalian subject who may be at risk of developing, a disease, disorder or condition, comprising:
   functionalizing a solid support to increase its affinity for a biomarker associated with a disease, disorder or condition;
   mixing, the functionalized solid support and a biological sample to form a test sample;
   providing a platform comprising at least one channel, a first electrode for sending a signal and a second electrode for receiving the signal;
   inserting the test sample into a channel of the platform;
   using multi-channel impedance responses from frequencies ranging from 600 kHz to 25 MHz to calculate an impedance of the test sample based on the signal sent by the first electrode and received by the second electrode when the test sample is located adjacent to the first and second electrodes, wherein the impedance value is used to distinguish between a solid support bound to a biomarker and a solid support without a biomarker bound thereto; and
   identifying the presence of the biomarker associated with a disease, disorder or condition based on the calculated impedance of the test sample;
   wherein the disease, disorder or condition is a disease, disorder or condition of the oral cavity.

2. The method according to claim 1, further comprising the step of quantifying the amount of biomarker in the test sample.

3. The method according to claim 1, further comprising the step of determining the risk associated with developing, a disease, disorder or condition based on the amount of biomarker in the test sample; wherein detection of aberrant levels of the biomarker indicates the presence of, or an elevated risk associated with developing, the disease, disorder or condition.

4. The method according to claim 1, wherein the solid support is selected from: a bead; a particle; a film; a slide; a zeolite; and a hydrogel.

5. The method according to claim 1, wherein the platform is a micro-fluidic biochip, wherein the channel, the first electrode, and the second electrode are formed on the micro-fluidic biochip.

6. The method according to claim 1, wherein the biomarker is selected from: APP; Cystatin A; Cystatin B; Cystatin C; Cystatin E/M; EMMPRIN; Fetuin B; HAI-1; HAI-2; HE4/WFDC2; Latexin; Lipocalin-1; Lipocalin-2/NGAL; RECK; Serpin A5; Serpin A8/AGT; Serpin A9/Centerin; Serpin A12; Serpin B5/Maspin; Serpin B6; Serpin B8; Serpin E1/PAI-1; Serpin F1/PEDF; Testican 1/SPOCK1; Testican 2/SPOCK2; TFPI; TFPI-2; TIMP-1; TIMP-2; TIMP-3; TIMP-4; Trappin-2/Elafin; Cathepsin B; Cathepsin C/DPPI; Cathepsin D; Cathepsin E; Cathepsin L; Cathepsin S; Cathepsin V; Cathepsin X/Z/P; DPPIV/CD26; Kallikrein 3/PSA; Kallikrein 5; Kallikrein 6; Kallikrein 7; Kallikrein 10; Kallikrein 11; Kallikrein 13; MMP-1; MMP-2; MMP-3; MMP-7; MMP-8; MMP-9; MMP-10; MMP-12; MMP-13; Neprilysin/CD10; Presenilin-1; Proprotein Convertase 9; Proteinase 3; uPA/Urokinase; ADAM8; ADAM9; ADAMTS1; ADAMTS13; Cathepsin A; ADAMTS1; Bcl-2; Carbonic Anhydrase IX; Cited-2; COX-2; Cytochrome c; Dkk-4; FABP1/L-FABP; HIF-1 alpha; HIF-2 alpha; Phospho-HSP27 (S78/S82); HSP60; HSP70; IDO; Phospho-JNK Pan (T183/Y185); NFkappaB1; p21/CIP1; p27/Kip1; Phospho-p38 alpha (T180/Y182); Phospho-p53 (S46); PON1; PON2; PON3; Thioredoxin-1; SIRT2; SOD2; Adiponectin/Acrp30; Angiogenin; Angiopoietin-1; Angiopoietin-2; Apolipoprotein A1; BAFF/BLyS/TNFSF13B; BDNF; CD14; CD30; CD31/PECAM-1; CD40 Ligand/TNFSF5; Chitinase 3-like; Complement Component C5/C5a; Complement Factor D; C-Reactive Protein/CRP; Cripto-1; Cystatin C; Dkk-1; DPPIV/CD26; EGF; CXCL5/ENA-78; Endoglin/CD105; Fas Ligand; FGF basic; KGF/FGF-7; FGF-19; Flt-3 Ligand; G-CSF; GDF-15; GM-CSF; CXCL1/GRO alpha; Growth Hormone (GH); HGF; ICAM-1/CD54; IFN-gamma; IGFBP-2; IGFBP-3; IL-1 alpha/IL-1F1; IL-1 beta/IL-1F2; IL-1ra/IL-1F3; IL-2; IL-3; IL-4; IL-5; IL-6; IL-8; IL-10; IL-11; IL-12 p70; IL-13; IL-15; IL-16; IL-17A; IL-18 BPa; IL-19; IL-22; IL-23; IL-24; IL-27; IL-31; IL-32 alpha/beta/gamm; IL-33; IL-34; CXCL10/IP-10; CXCL11/I-TAC; Kallikrein 3/PSA; Leptin; LIF; Lipocalin-2/NGAL; CCL2/MCP-1; CCL7/MCP-3; M-CSF; MIF; CXCL9/MIG; CCL3/CCL4 MIP-1 alpha/beta; CCL20/MIP-3 alpha; CCL19/MIP-3 beta; MMP-9; Myeloperoxidase; Osteopontin (OPN); PDGF-AA; PDGF-AB/BB; Pentraxin 3/TSF-14; CXCL4/PF4; RAGE; CCL5/RANTES; RBP; Relaxin-2; Resistin; CXCL12/SDF-1 alpha; Serpin E1/PAI-1; SHBG; ST2/IL1 R4; CCL17/TARC; TFF3; TfR; TGF-alpha; Thrombospondin-1; TIM-1; TNF-alpha; uPAR; VCAM-1; VEGF; Vitamin D BP; and a combination of two or more thereof.

7. The method according to claim 1, wherein the disease, disorder or condition of the oral cavity is selected from: gingivitis; periodontitis; a herpes simplex virus; candidiasis; a canker sore; caries; halitosis; xerostomia; and a combination of two or more thereof.

8. The method according to claim 1, wherein the biological sample comprises saliva, blood, urine, sweat, exhaled breath condensate, a tissue, or a combination thereof.

9. A biochip comprising:
a channel comprising an inlet for receiving a test sample, the test sample comprising a biological sample and a solid support having an increased affinity for a biomarker associated with a disease, disorder or condition;
a first electrode and a second electrode each positioned adjacent to the channel, the first electrode being configured to send a signal and the second electrode being configured to receive the signal; and
a processor configured to:
use multi-channel impedance responses from frequencies ranging from 600 kHz to 25 MHz to calculate an impedance value of the test sample from the signal sent by the first electrode and received by the second electrode, when the test sample is located adjacent to the first electrode and the second electrode, wherein the impedance value is used to distinguish between a solid support bound to a biomarker and a solid support without a biomarker bound thereto;
wherein the disease, disorder or condition is a disease, disorder or condition of the oral cavity.

10. The biochip according to claim 9, wherein the processor is further configured to quantify the amount of the biomarker associated with a disease, disorder or condition, based on the calculated impedance value of the test sample.

11. The biochip according to claim 9, wherein the solid support is selected from a bead; a particle; a film; a slide; a zeolite; and a hydrogel.

12. The biochip according to claim 9, wherein the biomarker is selected from: APP; Cystatin A; Cystatin B; Cystatin C; Cystatin E/M; EMMPRIN; Fetuin B; HAI-1; HAI-2; HE4/WFDC2; Latexin; Lipocalin-1; Lipocalin-2/NGAL; RECK; Serpin A5; Serpin A8/AGT; Serpin A9/Centerin; Serpin A12; Serpin B5/Maspin; Serpin B6; Serpin B8; Serpin E1/PAI-1; Serpin F1/PEDF; Testican 1/SPOCK1; Testican 2/SPOCK2; TFPI; TFPI-2; TIMP-1; TIMP-2; TIMP-3; TIMP-4; Trappin-2/Elafin; Cathepsin B; Cathepsin C/DPPI; Cathepsin D; Cathepsin E; Cathepsin L; Cathepsin S; Cathepsin V; Cathepsin X/Z/P; DPPIV/CD26; Kallikrein 3/PSA; Kallikrein 5; Kallikrein 6; Kallikrein 7; Kallikrein 10; Kallikrein 11; Kallikrein 13; MMP-1; MMP-2; MMP-3; MMP-7; MMP-8; MMP-9; MMP-10; MMP-12; MMP-13; Neprilysin/CD10; Presenilin-1; Proprotein Convertase 9; Proteinase 3; uPA/Urokinase; ADAM8; ADAM9; ADAMTS1; ADAMTS13; Cathepsin A; ADAMTS1; Bcl-2; Carbonic Anhydrase IX; Cited-2; COX-2; Cytochrome c; Dkk-4; FABP1/L-FABP; HIF-1 alpha; HIF-2 alpha; Phospho-HSP27 (S78/S82); HSP60; HSP70; IDO; Phospho-JNK Pan (T183/Y185); NFkappaB1; p21/CIP1; p27/Kip1; Phospho-p38 alpha (T180/Y182); Phospho-p53 (S46); PON1; PON2; PON3; Thioredoxin-1; SIRT2; SOD2; Adiponectin/Acrp30; Angiogenin; Angiopoietin-1; Angiopoietin-2; Apolipoprotein A1; BAFF/BLyS/TNFSF13B; BDNF; CD14; CD30; CD31/PECAM-1; CD40 Ligand/TNFSF5; Chitinase 3-like; Complement Component C5/C5a; Complement Factor D; C-Reactive Protein/CRP; Cripto-1; Cystatin C; Dkk-1; DPPIV/CD26; EGF; CXCL5/ENA-78; Endoglin/CD105; Fas Ligand; FGF basic; KGF/FGF-7; FGF-19; Flt-3 Ligand; G-CSF; GDF-15; GM-CSF; CXCL1/GRO alpha; Growth Hormone (GH); HGF; ICAM-1/CD54; IFN-gamma; IGFBP-2; IGFBP-3; IL-1 alpha/IL-1F1; IL-1 beta/IL-1F2; IL-1ra/IL-1F3; IL-2; IL-3; IL-4; IL-5; IL-6; IL-8; IL-10; IL-11; IL-12 p70; IL-13; IL-15; IL-16; IL-17A; IL-18 BPa; IL-19; IL-22; IL-23; IL-24; IL-27; IL-31; IL-32 alpha/beta/ gamm; IL-33; IL-34; CXCL10/IP-10; CXCL11/I-TAC; Kallikrein 3/PSA; Leptin; LIF; Lipocalin-2/NGAL; CCL2/MCP-1; CCL7/MCP-3; M-CSF; MIF; CXCL9/MIG; CCL3/CCL4 MIP-1 alpha/beta; CCL20/MIP-3 alpha; CCL19/MIP-3 beta; MMP-9; Myeloperoxidase; Osteopontin (OPN); PDGF-AA; PDGF-AB/BB; Pentraxin 3/TSF-14; CXCL4/PF4; RAGE; CCL5/RANTES; RBP; Relaxin-2; Resistin; CXCL12/SDF-1 alpha; Serpin E1/PAI-1; SHBG; ST2/IL1 R4; CCL17/TARC; TFF3; TfR; TGF-alpha; Thrombospondin-1; TIM-1; TNF-alpha; uPAR; VCAM-1; VEGF; Vitamin D BP; and a combination of two or more thereof.

13. The biochip according to claim 9, wherein the disease, disorder or condition of the oral cavity is selected from: gingivitis; periodontitis; a herpes simplex virus; candidiasis; a canker sore; caries; halitosis; xerostomia; and a combination of two or more thereof.

14. The biochip according to claim 9, wherein the biological sample comprises saliva, blood, urine, sweat, exhaled breath condensate, a tissue, or a combination thereof.

15. A method for identifying a mammalian subject suffering from, or at risk for developing, a disease, disorder or condition, comprising:
obtaining a biological sample from a mammalian subject;
functionalizing a solid support to increase its affinity for a biomarker associated with a disease, disorder or condition;
mixing, the functionalized solid support and the biological sample to form a test sample;
providing a platform comprising at least one channel, a first electrode for sending a signal and a second electrode for receiving the signal;
inserting the test sample into a channel of the platform;
using multi-channel impedance responses from frequencies ranging from 600 kHz to 25 MHz to calculate an impedance of the test sample based on the signal being sent by the first electrode and being received by the second electrode when the test sample is located adjacent to the first and second electrodes, wherein the impedance value is used to distinguish between a solid support bound to a biomarker and a solid support without a biomarker bound thereto;
quantifying the presence of the biomarker associated with a disease, disorder or condition based on the calculated impedance of the test sample;
wherein aberrant levels of the biomarker indicate the presence of, or an elevated risk associated with developing, a disease, disorder or condition;
wherein the disease, disorder or condition is a disease, disorder or condition of the oral cavity.

16. The method according to claim 15, wherein the biomarker is selected from: APP; Cystatin A; Cystatin B; Cystatin C; Cystatin E/M; EMMPRIN; Fetuin B; HAI-1; HAI-2; HE4/WFDC2; Latexin; Lipocalin-1; Lipocalin-2/NGAL; RECK; Serpin A5; Serpin A8/AGT; Serpin A9/Centerin; Serpin A12; Serpin B5/Maspin; Serpin B6; Serpin B8; Serpin E1/PAI-1; Serpin F1/PEDF; Testican 1/SPOCK1; Testican 2/SPOCK2; TFPI; TFPI-2; TIMP-1; TIMP-2; TIMP-3; TIMP-4; Trappin-2/Elafin; Cathepsin B; Cathepsin C/DPPI; Cathepsin D; Cathepsin E; Cathepsin L; Cathepsin S; Cathepsin V; Cathepsin X/Z/P; DPPIV/CD26; Kallikrein 3/PSA; Kallikrein 5; Kallikrein 6; Kallikrein 7; Kallikrein 10; Kallikrein 11; Kallikrein 13; MMP-1; MMP-2; MMP-3; MMP-7; MMP-8; MMP-9; MMP-10; MMP-12; MMP-13; Neprilysin/CD10; Presenilin-1; Proprotein Convertase 9; Proteinase 3; uPA/Urokinase; ADAM8; ADAM9; ADAMTS1; ADAMTS13; Cathepsin A; ADAMTS1; Bcl-2; Carbonic Anhydrase IX; Cited-2; COX-2; Cytochrome c; Dkk-4; FABP1/L-FABP; HIF-1 alpha; HIF-2 alpha; Phospho-HSP27 (S78/S82); HSP60; HSP70; IDO; Phospho-JNK Pan (T183/Y185); NFkappaB1; p21/CIP1; p27/Kip1; Phospho-p38 alpha (T180/Y182); Phospho-p53 (S46); PON1; PON2; PON3; Thioredoxin-1; SIRT2; SOD2; Adiponectin/Acrp30; Angiogenin; Angiopoietin-1; Angiopoietin-2; Apolipoprotein A1; BAFF/BLyS/TNFSF13B; BDNF; CD14; CD30; CD31/PECAM-1; CD40 Ligand/TNFSF5; Chitinase 3-like; Complement Component C5/C5a; Complement Factor D; C-Reactive Protein/CRP; Cripto-1; Cystatin C; Dkk-1; DPPIV/CD26; EGF; CXCL5/ENA-78; Endoglin/CD105; Fas Ligand; FGF basic; KGF/FGF-7; FGF-19; Flt-3 Ligand; G-CSF; GDF-15; GM-CSF; CXCL1/GRO alpha; Growth Hormone (GH); HGF; ICAM-1/CD54; IFN-gamma; IGFBP-2; IGFBP-3; IL-1 alpha/IL-1F1; IL-1 beta/IL-1F2; IL-1ra/IL-1F3; IL-2; IL-3; IL-4; IL-5; IL-6; IL-8; IL-10; IL-11; IL-12 p70; IL-13; IL-15; IL-16; IL-17A; IL-18 BPa; IL-19; IL-22; IL-23; IL-24; IL-27; IL-31; IL-32 alpha/beta/gamm; IL-33; IL-34; CXCL10/IP-10; CXCL11/I-TAC; Kallikrein 3/PSA; Leptin; LIF; Lipocalin-2/NGAL; CCL2/MCP-1; CCL7/MCP-3; M-CSF; MIF; CXCL9/MIG; CCL3/CCL4 MIP-1 alpha/beta; CCL20/MIP-3 alpha; CCL19/MIP-3 beta; MMP-9; Myeloperoxidase; Osteopontin (OPN); PDGF-AA; PDGF-AB/BB; Pentraxin 3/TSF-14; CXCL4/PF4; RAGE; CCL5/RANTES; RBP; Relaxin-2; Resistin; CXCL12/SDF-1 alpha; Serpin E1/PAI-1; SHBG; ST2/IL1 R4; CCL17/TARC; TFF3; TfR; TGF-alpha; Thrombospondin-1; TIM-1; TNF-alpha; uPAR; VCAM-1; VEGF; Vitamin D BP; and a combination of two or more thereof.

17. The method according to claim 15, wherein the biological sample comprises saliva, blood, urine, sweat, exhaled breath condensate, a tissue, or a combination thereof.

* * * * *